(12) United States Patent
Borowicz et al.

(10) Patent No.: US 8,618,048 B2
(45) Date of Patent: Dec. 31, 2013

(54) INSULIN ANALOGUES OF PROLONGED ACTIVITY

(75) Inventors: Piotr Borowicz, Warsaw (PL); Andrzej Plucienniczak, Warsaw (PL); Jerzy Mikolajczyk, Warsaw (PL); Tadeusz Glabski, Warsaw (PL); Dariusz Kurzynoga, Warsaw (PL); Diana Mikiewicz-Sygula, Warsaw (PL); Anna Wojtowicz-Krawiec, Warsaw (PL); Marcin Zielinski, Warsaw (PL); Malgorzata Kesik-Brodacka, Warsaw (PL); Violetta Adamczewska-Cecuda, Warsaw (PL); Iwona Sokolowska, Warsaw (PL); Grazyna Plucienniczak, Warsaw (PL); Dorota Stadnik, Warsaw (PL); Jaroslaw Antosik, Skierniewice (PL); Jacek Pstrzoch, Warsaw (PL); Justyna Bernat, Warsaw (PL); Wojciech Slawinski, Warsaw (PL); Tomasz Pawlukowiec, Deszno (PL); Jacek Stepniewski, Plock (PL); Monika Bogiel, Pruszkow (PL)

(73) Assignee: Instytut Biotechnologii I Antybiotyków, Warsaw (PL)

( * ) Notice: Subject to any disclaimer, the term of this patent is extended or adjusted under 35 U.S.C. 154(b) by 0 days.

(21) Appl. No.: 13/002,520

(22) PCT Filed: Jul. 4, 2009

(86) PCT No.: PCT/PL2009/050010
§ 371 (c)(1),
(2), (4) Date: Feb. 10, 2011

(87) PCT Pub. No.: WO2010/002283
PCT Pub. Date: Jan. 7, 2010

(65) Prior Publication Data
US 2011/0136736 A1 Jun. 9, 2011

(30) Foreign Application Priority Data
Jul. 4, 2008 (PL) .......................................... 385586

(51) Int. Cl.
*A61K 38/28* (2006.01)
(52) U.S. Cl.
USPC ............... 514/5.9; 514/6.1; 514/6.2; 514/6.4; 530/303; 530/304
(58) Field of Classification Search
None
See application file for complete search history.

(56) References Cited

U.S. PATENT DOCUMENTS

| | | |
|---|---|---|
| 4,959,351 A | 9/1990 | Grau |
| 5,506,202 A | 4/1996 | Vertesy et al. |
| 5,621,073 A | 4/1997 | Dickhardt et al. |
| 5,656,722 A | 8/1997 | Dorschug |
| 5,663,291 A | 9/1997 | Obermeier et al. |
| 5,977,297 A | 11/1999 | Obermeier et al. |
| 6,100,376 A | 8/2000 | Dorschug |
| 6,686,177 B1 | 2/2004 | Ertl et al. |
| 2002/0137144 A1 | 9/2002 | Kjeldsen et al. |
| 2008/0051336 A1 | 2/2008 | Bonaventure et al. |
| 2009/0099065 A1* | 4/2009 | Madsen et al. .................. 514/3 |

FOREIGN PATENT DOCUMENTS

| | | |
|---|---|---|
| EP | 0376156 A2 | 7/1990 |
| EP | 0 849 277 A2 | 6/1998 |
| WO | 9316724 A1 | 9/1993 |
| WO | 2004111244 A2 | 12/2004 |
| WO | 2005066344 A2 | 7/2005 |
| WO | 2006096079 A2 | 9/2006 |
| WO | 2008015099 A2 | 2/2008 |
| WO | 2008049931 A1 | 5/2008 |

\* cited by examiner

Primary Examiner — Elly-Gerald Stoica
(74) Attorney, Agent, or Firm — Christopher L. Parmelee; Walker & Jocke

(57) ABSTRACT

New biosynthetic analogues of recombined human insulin of prolonged therapeutical activity, which can find place in prophylactic and treatment of diabetes.

6 Claims, 14 Drawing Sheets

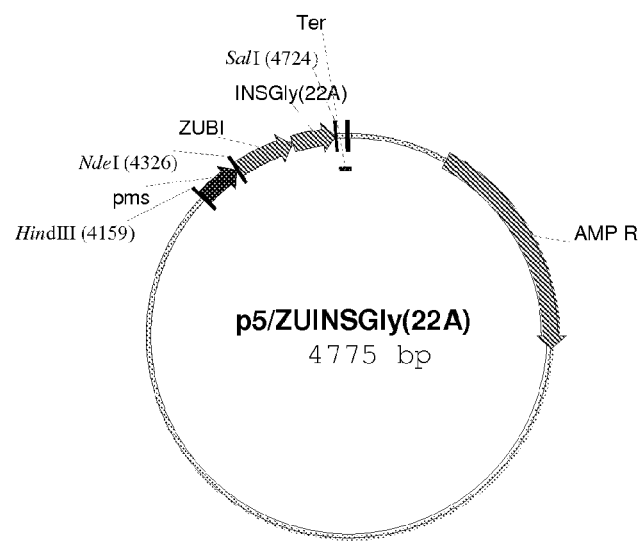

Fig. 1

Figure 3:
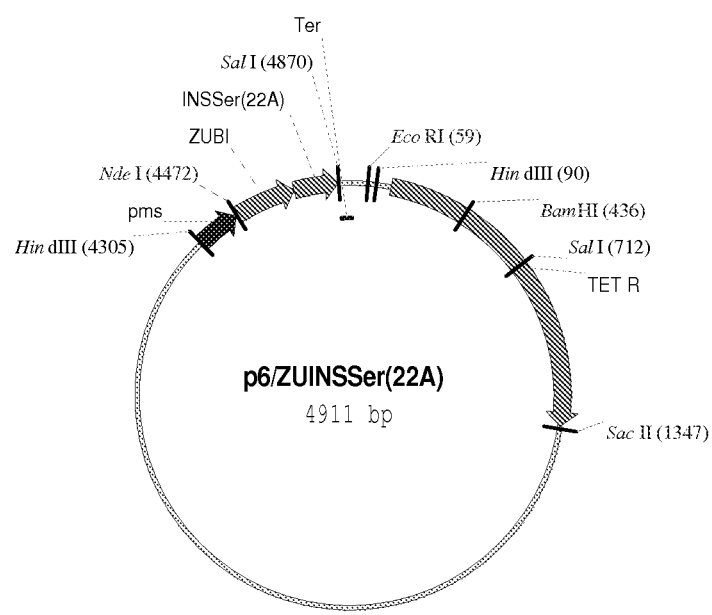

```
  1    TAGAGCGCAC GAATGAGGGC CGACAGGAAG CAAAGCTGAA AGGAATCAAA
       ATCTCGCGTG CTTACTCCCG GCTGTCCTTC GTTTCGACTT TCCTTAGTTT
 51    TTTGGCCGCA GGCGTACCGT GGACAGGAAC GTCGTGCTGA CGCTTCATCA
       AAACCGGCGT CCGCATGGCA CCTGTCCTTG CAGCACGACT GCGAAGTAGT
101    GAAGGGCACT GGTGCAACGG AAATTGCTCA TCAGCTCAGT ATTGCCCGCT
       CTTCCCGTGA CCACGTTGCC TTTAACGAGT AGTCGAGTCA TAACGGGCGA
151    CCACGGTTTA TAAAATTCTT GAAGACGAAA GGGCCTCGTG ATACGCCTAT
       GGTGCCAAAT ATTTTAAGAA CTTCTGCTTT CCCGGAGCAC TATGCGGATA
```

Fig. 2A

```
201  TTTTATAGGT TAATGTCATG ATAATAATGG TTTCTTAGAC GTCAGGTGGC
     AAAATATCCA ATTACAGTAC TATTATTACC AAAGAATCTG CAGTCCACCG
251  ACTTTCGGG  GAAATGTGCG CGGAACCCCT ATTTGTTTAT TTTTCTAAAT
     TGAAAAGCCC CTTTACACGC GCCTTGGGGA TAAACAAATA AAAAGATTTA
301  ACATTCAAAT ATGTATCCGC TCATGAGACA ATAACCCTGA TAAATGCTTC
     TGTAAGTTTA TACATAGGCG AGTACTCTGT TATTGGGACT ATTTACGAAG
351  AATAATATTG AAAAAGGAAG AGTATGAGTA TTCAACATTT CCGTGTCGCC
     TTATTATAAC TTTTTCCTTC TCATACTCAT AAGTTGTAAA GGCACAGCGG
401  CTTATTCCCT TTTTTGCGGC ATTTTGCCTT CCTGTTTTTG CTCACCCAGA
     GAATAAGGGA AAAAACGCCG TAAAACGGAA GGACAAAAAC GAGTGGGTCT
451  AACGCTGGTG AAAGTAAAAG ATGCTGAAGA TCAGTTGGGT GCACGAGTGG
     TTGCGACCAC TTTCATTTTC TACGACTTCT AGTCAACCCA CGTGCTCACC
501  GTTACATCGA ACTGGATCTC AACAGCGGTA AGATCCTTGA GAGTTTTCGC
     CAATGTAGCT TGACCTAGAG TTGTCGCCAT TCTAGGAACT CTCAAAAGCG
551  CCCGAAGAAC GTTTTCCAAT GATGAGCACT TTTAAAGTTC TGCTATGTGG
     GGGCTTCTTG CAAAAGGTTA CTACTCGTGA AAATTTCAAG ACGATACACC
601  CGCGGTATTA TCCCGTGTTG ACGCCGGGCA AGAGCAACTC GGTCGCCGCA
     GCGCCATAAT AGGGCACAAC TGCGGCCCGT TCTCGTTGAG CCAGCGGCGT
651  TACACTATTC TCAGAATGAC TTGGTTGAGT ACTCACCAGT CACAGAAAAG
     ATGTGATAAG AGTCTTACTG AACCAACTCA TGAGTGGTCA GTGTCTTTTC
701  CATCTTACGG ATGGCATGAC AGTAAGAGAA TTATGCAGTG CTGCCATAAC
     GTAGAATGCC TACCGTACTG TCATTCTCTT AATACGTCAC GACGGTATTG
751  CATGAGTGAT AACACTGCGG CCAACTTACT TCTGACAACG ATCGGAGGAC
     GTACTCACTA TTGTGACGCC GGTTGAATGA AGACTGTTGC TAGCCTCCTG
801  CGAAGGAGCT AACCGCTTTT TTGCACAACA TGGGGGATCA TGTAACTCGC
     GCTTCCTCGA TTGGCGAAAA AACGTGTTGT ACCCCCTAGT ACATTGAGCG
851  CTTGATCGTT GGGAACCGGA GCTGAATGAA GCCATACCAA ACGACGAGCG
     GAACTAGCAA CCCTTGGCCT CGACTTACTT CGGTATGGTT TGCTGCTCGC
901  TGACACCACG ATGCCTGCAG CAATGGCAAC AACGTTGCGC AAACTATTAA
     ACTGTGGTGC TACGGACGTC GTTACCGTTG TTGCAACGCG TTTGATAATT
951  CTGGCGAACT ACTTACTCTA GCTTCCCGGC AACAATTAAT AGACTGGATG
     GACCGCTTGA TGAATGAGAT CGAAGGGCCG TTGTTAATTA TCTGACCTAC
1001 GAGGCGGATA AAGTTGCAGG ACCACTTCTG CGCTCGGCCC TTCCGGCTGG
     CTCCGCCTAT TTCAACGTCC TGGTGAAGAC GCGAGCCGGG AAGGCCGACC
1051 CTGGTTTATT GCTGATAAAT CTGGAGCCGG TGAGCGTGGG TCTCGCGGTA
     GACCAAATAA CGACTATTTA GACCTCGGCC ACTCGCACCC AGAGCGCCAT
1101 TCATTGCAGC ACTGGGGCCA GATGGTAAGC CCTCCCGTAT CGTAGTTATC
     AGTAACGTCG TGACCCCGGT CTACCATTCG GGAGGGCATA GCATCAATAG
1151 TACACGACGG GGAGTCAGGC AACTATGGAT GAACGAAATA GACAGATCGC
     ATGTGCTGCC CCTCAGTCCG TTGATACCTA CTTGCTTTAT CTGTCTAGCG
1201 TGAGATAGGT GCCTCACTGA TTAAGCATTG GTAACTGTCA GACCAAGTTT
     ACTCTATCCA CGGAGTGACT AATTCGTAAC CATTGACAGT CTGGTTCAAA
1251 ACTCATATAT ACTTTAGATT GATTTAAAAC TTCATTTTTA ATTTAAAAGG
     TGAGTATATA TGAAATCTAA CTAAATTTTG AAGTAAAAAT TAAATTTTCC
1301 ATCTAGGTGA AGATCCTTTT TGATAATCTC ATGACCAAAA TCCCTTAACG
     TAGATCCACT TCTAGGAAAA ACTATTAGAG TACTGGTTTT AGGGAATTGC
1351 TGAGTTTTCG TTCCACTGAG CGTCAGACCC CATCGCCGTT CTCGATACGC
     ACTCAAAAGC AAGGTGACTC GCAGTCTGGG GTAGCGGCAA GAGCTATGCG
1401 TGAACCGTGC GCACGCTCAT CCCGGACAGT TCAGCAAGCT GCTCCTGGGA
     ACTTGGCACG CGTGCGAGTA GGGCCTGTCA AGTCGTTCGA CGAGGACCCT
1451 CCAGGCACGC GCAAGACGCA GCGACCTGAA TTTGTTGGTA TCACTCATTT
     GGTCCGTGCG CGTTCTGCGT CGCTGGACTT AAACAACCAT AGTGAGTAAA
1501 CCTGTCTCCG AATGGAAGAT GGTCACCACA CACTCTTGAC CGCGTAATCC
     GGACAGAGGC TTACCTTCTA CCAGTCGTGT GTGAGAACTG GCGCATTAGG
1551 TGCGCGACCA CGATCTTAAC CCGACAGTAA CGTGACAGCG GTCTGACATG
     ACGCGCTGGT GCTAGAATTG GGCTGTCATT GCACTGTCGC CAGACTGTAC
1601 CCGCATTGAG GTCTTTGAAA CCGTAACTTC AGAAGCATGT ACGGTCAGAT
     GGCGTAACTC CAGAAACTTT GGCATTGAAG TCTTCGTACA TGCCAGTCTA
1651 TTAACATAAG AGTTCATTGT ACGCACCGTT AAAACGCGCT CAGCGCGCTT
     AATTGTATTC TCAAGTAACA TGCGTGGCAA TTTTGCGCGA GTCGCGCGAA
```

Fig. 2B

```
1701  CTGGCGCAAA AACCGTAAAA ATGGATGTTT TCCCCCGGGT AAACCGGAAA
      GACCGCGTTT TTGGCATTTT TACCTACAAA AGGGGGCCCA TTTGGCCTTT
1751  AATGCGTCAG GAACGCTTTC AGCGCGTTGC ATGACTATGC ATGAAACTGA
      TTACGCAGTC CTTGCGAAAG TCGCGCAACG TACTGATACG TACTTTGACT
1801  ATGGCGATCG GTTTGGGCGC GTCTGATGCC CATAAGGCGT ATTTTCGGAC
      TACCGCTAGC CAAACCCGCG CAGACTACGG GTATTCCGCA TAAAAGCCTG
1851  GTTTTCAGCC CTGATAAGAA GAAATCAGAC TGTAGTTACA GACGAGTCGT
      CAAAAGTCGG GACTATTCTT CTTTAGTCTG ACATCAATGT CTGCTCAGCA
1901  GAGCGATTCA CTACGGGAGT CGTCGGCGAG TCATCCAGTA TTTTTCCTCG
      CTCGCTAAGT GATGCCCTCA GCAGCCGCTC AGTAGGTCAT AAAAAGGAGC
1951  CGACTCTCTG GCGACTCGCC TTCTCTGAAC ACCAGAGCGA CAGTGTGTTG
      GCTGAGAGAC CGCTGAGCGG AAGAGACTTG TGGTCTCGCT GTCACACAAC
2001  AGTCATCGAT AAATCACCGA CGACTCGTTG CCGAGTCATC CAGTAGTCGC
      TCAGTAGCTA TTTAGTGGCT GCTGAGCAAC GGCTCAGTAG GTCATCAGCG
2051  CGACGAGCCG CTTTTGTATA AATCCGAATA AGAAAATATA TTTTTCAAAC
      GCTGCTCGGC GAAAACATAT TTAGGCTTAT TCTTTTATAT AAAAAGTTTG
2101  CATAACAACA TGATTTAAAA AGCAAATCAG AAAAAAGTTA GTTTTGCGTG
      GTATTGTTGT ACTAAATTTT TCGTTTAGTC TTTTTTCAAT CAAAACGCAC
2151  GGGTGTGGGC ATCCTGGGAA TGAGAACAGA CTCGCGTTTT TCTGGAGGAA
      CCCACACCCG TAGGACCCTT ACTCTTGTCT GAGCGCAAAA AGACCTCCTT
2201  CTGCGGGGAT TTTGATTAA ACAATAGTCA CCGCAGAGCG GAATTTTATG
      GACGCCCCTA AAAACTAATT TGTTATCAGT GGCGTCTCGC CTTAAAATAC
2251  CAACGCTGGC TGTGCGGCAC GGGGATTTTT AATCCCCCGG CCCGTTATTC
      GTTGCGACCG ACACGCCGTG CCCCTAAAAA TTAGGGGGCC GGGCAATAAG
2301  ATCTCCACGG GCGACGGGGA TACATAAACC CGACAGCAGA GGACGGGTGA
      TAGAGGTGCC CGCTGCCCCT ATGTATTGG GCTGTCGTCT CCTGCCCACT
2351  GCGCGAATCC CAGAGATGAT GAAAAAAGAG GCAGAGAAAC GCGCCCAGGT
      CGCGCTTAGG GTCTCTACTA CTTTTTTCTC CGTCTCTTTG CGCGGGTCCA
2401  ACGTTTTATC TTATTGCTTT GGTGTTGTCC AGGGTGTCGG GGCTGTGCCC
      TGCAAAATAG AATAACGAAA CCACAACAGG TCCCACAGCC CCGACACGGG
2451  TGACCAGGTG GCATTTGTCT GATTGCGCGT GCGCGGTCCG ACAAATGCAC
      ACTGGTCCAC CGTAAACAGA CTAACGCGCA CGCGCCAGGC TGTTTACGTG
2501  ATCCTGCCCC GTCCTGTACG TGTTTTTTTC ACCAGAACAA CTTCACGAAG
      TAGGACGGGG CAGGACATGC ACAAAAAAAG TGGTCTTGTT GAAGTGCTTC
2551  TGGCGGATGA ACGCTACCAA CGTTGCCGGG AACGCTTCGG CGATGATGGC
      ACCGCCTACT TGCGATGGTT GCAACGGCCC TTGCGAAGCC GCTACTACCG
2601  ATAACGGGCT GATACAGGCA GCTCCCGGAG ACGGACACAG CTTGCCTGTG
      TATTGCCCGA CTATGTCCGT CGAGGGCCTC TGCCTGTGTC GAACGGACAC
2651  AGCGGATGCC GGGAGCCGAC AAGCCCGTCA GGGCGCGTCA GCGGGTTTTA
      TCGCCTACGG CCCTCGGCTG TTCGGGCAGT CCCGCGCAGT CGCCCAAAAT
2701  GCGGGTGTCG GGGCGCAGCC ATGACCCAGT CACGTAGCGA TAGCGGAGTG
      CGCCCACAGC CCCGCGTCGG TACTGGGTCA GTGCATCGCT ATCGCCTCAC
2751  TATACTGGCT AATATGTTA AATCGGAGTG GTAATTCAGG GAAGTGCTTC
      ATATGACCGA ATTATACAAT TTAGCCTCAC CATTAAGTCC CTTCACGAAG
2801  ATGTGGCAAA GGAAAATGT GGCTATCGTG CGTAAGTGCA ACATGTAGGT
      TACACCGTTT CCTTTTTACA CCGATAGCAC GCATTCACGT TGTACATCCA
2851  AAAGGTGAAA TGACGCCTCC TCGCTCACTC GGTCGCTACG CTCCTGCCGT
      TTTCCACTTT ACTGCGGAGG AGCGAGTGAG CCAGCGATGC GAGGACGGCA

2901  GAGACTGCGG CGGGCGTTAC CGGCTCACAA ATAACGGGAT ACGCAGGCAG
      CTCTGACGCC GCCCGCAATG GCCGAGTGTT TATTGCCCTA TGCGTCCGTC
2951  TGCTCAAATC AGGAAGGACC GGAAAAAGGA TGCGGCGTAG CCGTTTTTCC
      ACGAGTTTAG TCCTTCCTGG CCTTTTTCCT ACGCCGCATC GGCAAAAAGG
3001  ATAGGCTCCG CCCCCCTGAC AAGCATCACG AAATCTGACG CTCAAATCAG
      TATCCGAGGC GGGGGGACTG TTCGTAGTGC TTTAGACTGC GAGTTTAGTC
3051  TGGCGGCGAA ACCCGACAGG ACTATAAAGA TCCCAGGCGT TTCCCCCTGG
      ACCGCCGCTT TGGGCTGTCC TGATATTTCT AGGGTCCGCA AAGGGGGACC
```

Fig. 2C

```
3101  TAGCTCCCTC GTGCGCTCTC CTGTTCCTGC CTTTCGGTTT ACCGGTGTCA
      ATCGAGGGAG CACGCGAGAG GACAAGGACG GAAAGCCAAA TGGCCACAGT
3151  TTCCGCTGTT ATGGCCGCGT TTGTCTCATT CCACGCCTGA CACTCAGTTC
      AAGGCGACAA TACCGGCGCA AACAGAGTAA GGTGCGGACT GTGAGTCAAG
3201  CGGGTAGGCA GTTCGCTCCA AGCTGGACTG TATGCACGAA CCCCCCGTTC
      GCCCATCCGT CAAGCGAGGT TCGACCTGAC ATACGTGCTT GGGGGGCAAG
3251  AGTCCGACTA CCACGCCCGT TCCGGTAACT ATCAACTTGA GTCCAACCCG
      TCAGGCTGAT GGTGCGGGCA AGGCCATTGA TAGTTGAACT CAGGTTGGGC
3301  GAAAGACACG ACAAATCGCC AGTGGCGGTA GCCATTGGTA ACTGAGATGT
      CTTTCTGTGC TGTTTAGCGG TCACCGCCAT CGGTAACCAT TGACTCTACA
3351  CCCACAGATT TATCTGGAGT TCTTGAACTC GGGGCCTCAG TCCGGCTACA
      CGCTCTCTAA ATAGACCTCA AGAACTTCAC CCCCGGACTC ACGCCGATGT
3401  CTGGAAGGAC AGTTAGGTG ACTCGTCTCG CACAAGACAG TTACCAGGTT
      GACCTTCCTG TCAAATCCAC TGAGCAGAGC GTGTTCTGTC AATGGTCCAA
3451  AAGCAGTTCC CCAACTGACC TAACCTTCGA TCAAACCACC TCCCCAGGTG
      TTCGTCAAGG GGTTGACTGG ATTGGAAGCT AGTTGGTGG AGGGGTCCAC
3501  GTTTTTTCCT TTTCAGACCA ACAGATTACC CGCACAAAAA AAGGATCTCA
      CAAAAAAGCA AAAGTCTCGT TGTCTAATGC GCGTCTTTTT TTCCTAGAGT
3551  AGAAGATCCT TTTTACAGGA GCGATTATCG TCTTCATCCA TGAAGGCGTT
      TCTTCTAGGA AAAATGTCCT CGCTAATAGC AGAAGTAGGT ACTTCCGCAA
3601  TGAAGATTAA ACCGGCCTAT TTCATAGATC GTAAAATCAG GGTTTGGGA
      ACTTCTAATT TGGCCGGATA AAGTATCTAG CATTTTAGTC CCAAAACCCT
3651  TGGCCGATGA AACCCCATAA AAACCCATAA ATACATACAC CTACTAACAA
      ACCGGCTACT TGGGGTATT TTTGGGTATT TATGTATGTG GATGATTGTT
3701  TCATCTTTTG CTGTACCAGG GTATGAAAAG TCTCAGGGTT CCACCCCAGA
      AGTAGAAAAC GACATGGTCC CATACTTTTC AGAGTCCCAA GGTGGGGTCT
3751  ATACGCCATC AACAAGTCCT GTCACACCGC AAATAACAT GCAAAAAATT
      TATGCGGTAG TTGTTCAGGA CAGTGTGGCG GTTATTGTA CGTTTTTAA
3801  GCGGATGACC GTAATCCGGG GTGCAGATCA ATGACTGAGA CAAGTATAAA
      CGCCTACTGG CATTAGGCCC CACGTCTAGT TACTGACTCT GTTCATATTT
3851  CTTCATGCAA AAAGTAATTA CAATCAGTCC CAAAGTCAGC GGTGTCCCGG
      GAAGTACGTT TTTCATTAAT GTTAGTCAGG GTTTCAGTCG CCACAGGGCC
3901  CCCTGATAAT CATGCCCGGA TTATCTGAAT TTCTCAGCGG GGGCTGTGAG
      GGGACTATTA GTACGGGCCT AATAGACTTA AAGAGTCGCC CCCGACACTC
3951  CGCCACAACC TGTATCCAAG AGCGGTGCCT ACGAGCAGTC CTGCCGTCAT
      GCGGTGTTGG ACATAGGTTC TCGCCACGGA TGCTCGTCAG GACGGCAGTA
4001  CATTGTAAGG CTTACGCCAG CAAGTTTTGT CTCAGTGATA ACACCTTATG
      GTAACATTCC GAATGCGGTC GTTCAAAACA GAGTCACTAT TGTGGAATAC
4051  CTCCCCATAC AAGGAAAAGT ATCGGGAGAA AAAACAAACG CCCGGTTGTC
      GAGGGGTATG TTCCTTTTCA TAGCCCTCTT TTTTGTTTGC GGGCCAACAG
4101  ATCTCCCGGT CATAAAGAGC AGCAAAACCG CGTCGTAGTA AAAAAGCCAG
      TAGAGGGCCA GTATTTCTCG TCGTTTTGGC GCAGCATCAT TTTTTCGGTC
4151  CAGGATCAAG CTTCAGGGTT GAGATGTGTA TAAGAGACAG ACTCTAGCCA
      GTCCTAGTTC GAAGTCCCAA CTCTACACAT ATTCTCTGTC TGAGATCGGT
4201  GTTCCAAGT AGAAACTACA GTTCTAAAC TGCAACTTTT TCTACTTTT
      CAAGGTTCA TCTTTGATGT CAAAGATTTG ACGTTGAAAA AGATGAAAAA
4251  GCAACTTAAT CTATTGACTA GTCCTTTATA AATGTTAAAA CATATATATA
      CGTTGAATTA GATAACTGAT CAGGAAATAT TTACAATTTT GTATATATAT
                                            Met GlnIlePheValLysThrLeu
4301  GAAATAAATA AAAAGAGGAG GTTCATATGC AAATTTTTGT TAAAACTTTA
      CTTTATTTAT TTTTCTCCTC CAAGTATACG TTTAAAAACA ATTTTGAAAT
      ThrGlyLys ThrIleThrLeu GluValGlu SerSerAspThr IleAspAsn·
4351  ACTGGTAAAA CCATTACCTT AGAAGTTGAA TCTTCAGATA CCATTGATAA

TGACCATTTT GGTAATGGAA TCTTCAACTT AGAAGTCTAT GGTAACTATT
  ·AsnValLysSer LysIleGln AspLysGlu GlyIleProPro AspGlnGlnAla·
4401  TGTTAAATCT AAAATTCAAG ATAAAGAAGG TATTCCTCCA GATCAACAAG
```

Fig. 2D

```
              ACAATTTAGA TTTTAAGTTC TATTTCTTCC ATAAGGAGGT CTAGTTGTTC
            ·AlaLeuIle PheAlaGlyLys GlnLeuGlu AspGlyAla ThrLeuSerAsp
     4451   CTCTAATATT TGCAGGTAAA CAGTTAGAAG ATGGTGCTAC CCTGTCTGAT
              GAGATTATAA ACGTCCATTT GTCAATCTTC TACCACGATG GGACAGACTA
              TyrAsnIleGln LysGluSer ThrLeuHis LeuValLeuAla LeuAlaGly·
     4501   TATAACATTC AGAAAGAATC TACCTTACAT CTGGTCTTAG CTCTCGCTGG
              ATATTGTAAG TCTTTCTTAG ATGGAATGTA GACCAGAATC GAGAGCGACC
            ·GlyGlyArgPhe ValAsnGlnHis LeuCysGly SerHisLeu ValGluAlaLeu·
     4551   TGGTCGTTTT GTCAACCAGC ACCTGTGTGG TTCTCACCTG GTTGAAGCAC
              ACCAGCAAAA CAGTTGGTCG TGGACACACC AAGAGTGGAC CAACTTCGTG
            ·LeuTyrLeuVal CysGlyGlu ArgGlyPhe PheTyrThrPro LysThrLys
     4601   TGTACCTGGT ATGTGGCGAA CGTGGTTTCT TCTACACTCC TAAAACAAAG
              ACATGGACCA TACACCGCTT GCACCAAAGA AGATGTGAGG ATTTTGTTTC
              ArgGlyIle ValGluGln CysCysThrSer IleCysSer LeuTyrGlnLeu·
     4651   CGCGGCATCG TTGAACAGTG CTGTACCTCT ATCTGTTCCC TGTACCAACT
              GCGCCGTAGC AACTTGTCAC GACATGGAGA TAGACAAGGG ACATGGTTGA
              ·LeuGluAsnTyr CysAsnGly ***
     4701   GGAGAACTAC TGCAATGGTT AAGTCGACTC TAGCTACAGC CTCCTTTCGG
              CCTCTTGATG ACGTTACCAA TTCAGCTGAG ATCGATGTCG GAGGAAAGCC
     4751   AGGCTGTTTT TTATCTCGAG GATCC
              TCCGACAAAA AATAGAGCTC CTAGG
```

Fig. 2E

```
   1    ATTATCATGA CATTAACCTA TAAAAATAGG CGTATCACGA GGCCCTTTCG
        TAATAGTACT GTAATTGGAT ATTTTTATCC GCATAGTGCT CCGGGAAAGC
  51    TCTTCAAGAA TTCTCATGTT TGACAGCTTA TCATCGATAA GCTTTAATGC
        AGAAGTTCTT AAGAGTACAA ACTGTCGAAT AGTAGCTATT CGAAATTACG
 101    GGTAGTTTAT CACAGTTAAA TTGCTAACGC AGTCAGGCAC CGTGTATGAA
        CCATCAAATA GTGTCAATTT AACGATTGCG TCAGTCCGTG GCACATACTT
 151    ATCTAACAAT GCGCTCATCG TCATCCTCGG CACCGTCACC CTGGATGCTG
        TAGATTGTTA CGCGAGTAGC AGTAGGAGCC GTGGCAGTGG GACCTACGAC
 201    TAGGCATAGG CTTGGTTATG CCGGTACTGC CGGGCCTCTT GCGGGATATC
        ATCCGTATCC GAACCAATAC GGCCATGACG GCCCGGAGAA CGCCCTATAG
 251    GTCCATTCCG ACAGCATCGC CAGTCACTAT GGCGTGCTGC TAGCGCTATA
        CAGGTAAGGC TGTCGTAGCG GTCAGTGATA CCGCACGACG ATCGCGATAT
 301    TGCGTTGATG CAATTTCTAT GCGCACCCGT TCTCGGAGCA CTGTCCGACC
        ACGCAACTAC GTTAAAGATA CGCGTGGGCA AGAGCCTCGT GACAGGCTGG
 351    GCTTTGGCCG CCGCCCAGTC CTGCTCGCTT CGCTACTTGG AGCCACTATC
        CGAAACCGGC GGCGGGTCAG GACGAGCGAA GCGATGAACC TCGGTGATAG
 401    GACTACGCGA TCATGGCGAC CACACCCGTC CTGTGGATCC TCTACGCCGG
        CTGATGCGCT AGTACCGCTG GTGTGGGCAG GACACCTAGG AGATGCGGCC
 451    ACGCATCGTG GCCGGCATCA CCGGCGCCAC AGGTGCGGTT GCTGGCGCCT
        TGCGTAGCAC CGGCCGTAGT GGCCGCGGTG TCCACGCCAA CGACCGCGGA
 501    ATATCGCCGA CATCACCGAT GGGGAAGATC GGGCTCGCCA CTTCGGGCTC
        TATAGCGGCT GTAGTGGCTA CCCCTTCTAG CCCGAGCGGT GAAGCCCGAG
 551    ATGAGCGCTT GTTTCGGCGT GGGTATGGTG GCAGGCCCCG TGGCCGGGGG
        TACTCGCGAA CAAAGCCGCA CCCATACCAC CGTCCGGGGC ACCGGCCCCC
 601    ACTGTTGGGC GCCATCTCCT TGCATGCACC ATTCCTTGCG GCGGCGGTGC
        TGACAACCCG CGGTAGAGGA ACGTACGTGG TAAGGAACGC CGCCGCCACG
 651    TCAACGGCCT CAACCTACTA CTGGGCTGCT TCCTAATGCA GGAGTCGCAT
        AGTTGCCGGA GTTGGATGAT GACCCGACGA AGGATTACGT CCTCAGCGTA
 701    AAGGGAGAGC GTCGACCGAT GCCCTTGAGA GCCTTCAACC CAGTCAGCTC
        TTCCCTCTCG CAGCTGGCTA CGGGAACTCT CGGAAGTTGG GTCAGTCGAG
 751    CTTCCGGTGG GCGCGGGGCA TGACTATCGT CGCCGCACTT ATGACTGTCT
        GAAGGCCACC CGCGCCCCGT ACTGATAGCA GCGGCGTGAA TACTGACAGA
 801    TCTTTATCAT GCAACTCGTA GGACAGGTGC CGGCAGCGCT CTGGGTCATT
        AGAAATAGTA CGTTGAGCAT CCTGTCCACG GCCGTCGCGA GACCCAGTAA
 851    TTCGGCGAGG ACCGCTTTCG CTGGAGCGCG ACGATGATCG GCCTGTCGCT
        AAGCCGCTCC TGGCGAAAGC GACCTCGCGC TGCTACTAGC CGGACAGCGA
 901    TGCGGTATTC GGGATCTTGC ACGCCCTCGC TCAAGCCTTC GTCACTGGTC
        ACGCCATAAG CCCTAGAACG TGCGGGAGCG AGTTCGGAAG CAGTGACCAG
 951    CCGCCACCAA ACGTTTCGGC GAGAAGCAGG CCATTATCGC CGGCATGGCG
        GGCGGTGGTT TGCAAAGCCG CTCTTCGTCC GGTAATAGCG GCCGTACCGC
1001    GCCGACGCGC TGGGCTACGA CTTGCTGGCG TTCGCGACGC GAGGCTGGAT
        CGGCTGCGCG ACCCGATGCA GAACGACCGC AAGCGCTGCG CTCCGACCTA
1051    GGCCTTCCCC ATTATGATTC TTCTCGCTTC CGGCGGCATC GGGATGCCCG
        CCGGAAGGGG TAATACTAAG AAGAGCGAAG GCCGCCGTAG CCCTACGGGC
1101    CGTTGCAGGC CATGCTGTCC AGGCAGGTAG ATGACGACCA TCAGGGACAG
        GCAACGTCCG GTACGACAGG TCCGTCCATC TACTGCTGGT AGTCCCTGTC
1151    CTTCAAGGAT CGCTCGCGGC TCTTACCAGC CTAACTTCGA TCATTGGACC
        GAAGTTCCTA GCGAGCGCCG AGAATGGTCG GATTGAAGCT AGTAACCTGG
1201    GCTGATCGTC ACGGCGATTT ATGCCGCCTC GGCGAGCACA TGGAACGGGT
        CGACTAGCAG TGCCGCTAAA TACGGCGGAG CCGCTCGTGT ACCTTGCCCA
1251    TGGCATGGAT TGTAGGCGCC GCCCTATACC TTGTCTGCCT CCCCGCGTTG
        ACCGTACCTA ACATCCGCGG CGGGATATGG AACAGACGGA GGGGCGCAAC
1301    CGTCGCGGTG CATGGAGCCG GGCCACCTCG ACCTGAATGG AACCGCGGAG
        GCAGCGCCAC GTACCTCGGC CCGGTGGAGC TGGACTTACC TTGGCGCCTC
1351    ATAGGTGCCT CACTGATTAA GCATTGGTAA CTGTCAGACC AAGTTTACTC
        TATCCACGGA GTGACTAATT CGTAACCATT GACAGTCTGG TTCAAATGAG
```

Fig. 4A

```
1401  ATATATACTT TAGATTGATT TAAAACTTCA TTTTTAATTT AAAAGGATCT
      TATATATGAA ATCTAACTAA ATTTTGAAGT AAAAATTAAA TTTTCCTAGA
1451  AGGTGAAGAT CCTTTTTGAT AATCTCATGA CCAAAATCCC TTAACGTGAG
      TCCACTTCTA GGAAAAACTA TTAGAGTACT GGTTTTAGGG AATTGCACTC
1501  TTTTCGTTCC ACTGAGCGTC AGACCCCATC GCCGTTCTCG ATACGCTGAA
      AAAAGCAAGG TGACTCGCAG TCTGGGGTAG CGGCAAGAGC TATGCGACTT
1551  CCGTGCGCAC GCTCATCCCG GACAGTTCAG CAAGCTGCTC CTGGGACCAG
      GGCACGCGTG CGAGTAGGGC CTGTCAAGTC GTTCGACGAG GACCCTGGTC
1601  GCACGCGCAA GACGCAGCGA CCTGAATTTG TTGGTATCAC TCATTTCCTG
      CGTGCGCGTT CTGCGTCGCT GGACTTAAAC AACCATAGTG AGTAAAGGAC
1651  TCTCCGAATG GAAGATGGTC AGCACACAGT GTTGACCGCG TAATCCTGCG
      AGAGGCTTAC CTTCTACCAG TCGTGTGTCA CAACTGGCGC ATTAGGACGC
1701  CGACCACGAT CTTAACCCGA CAGTAACGTG ACAGCGGTCT GACATGCCGC
      GCTGGTGCTA GAATTGGGCT GTCATTGCAC TGTCGCCAGA CTGTACGGCG
1751  ATTGAGGTCT TTGAAACCGT AACTTCAGAA GCATGTACGG TCAGATTTAA
      TAACTCCAGA AACTTTGGCA TTGAAGTCTT CGTACATGCC AGTCTAAATT
1801  CATAAGAGTT CATTGTACGC ACCGTTAAAA CGCGCTCAGC GCGCTTCTGG
      GTATTCTCAA GTAACATGCG TGGCAATTTT GCGCGAGTCG CGCGAAGACC
1851  CGCAAAAACC GTAAAAATGG ATGTTTTCCC CCGGGTAAAC CGGAAAAATG
      GCGTTTTTGG CATTTTTACC TACAAAAGGG GGCCCATTTG GCCTTTTTAC
1901  CGTCAGGAAC GCTTTCAGCG CGTTGCATGA CTATGCATGA AACTGAATGG
      GCAGTCCTTG CGAAAGTCGC GCAACGTACT GATACGTACT TTGACTTACC
1951  CGATCGGTTT GGGCGCGTCT GATGCCCATA AGGCGTATTT TCGGACGTTT
      GCTAGCCAAA CCCGCGCAGA CTACGGGTAT TCCGCATAAA AGCCTGCAAA
2001  TCAGCCCTGA TAAGAAGAAA TCAGACTGTA GTTACAGACG AGTCGTGAGC
      AGTCGGGACT ATTCTTCTTT AGTCTGACAT CAATGTCTGC TCAGCACTCG
2051  GATTCACTAC GGGAGTCGTC GGCGAGTCAT CCAGTATTTT TCCTCGCGAC
      CTAAGTGATG CCCTCAGCAG CCGCTCAGTA GGTCATAAAA AGGAGCGCTG
2101  TCTCTGGCGA CTCGCCTTCT CTGAACACCA GAGCGACAGT GTGTTGAGTC
      AGAGACCGCT GAGCGGAAGA GACTTGTGGT CTCGCTGTCA CACAACTCAG
2151  ATCGATAAAT CACCGACGAC TCGTTGCCGA GTCATCCAGT AGTCGCCGAC
      TAGCTATTTA GTGGCTGCTG AGCAACGGCT CAGTAGGTCA TCAGCGGCTG
2201  GAGCCGCTTT TGTATAAATC CGAATAAGAA AATATATTTT TCAAACCATA
      CTCGGCGAAA ACATATTTAG GCTTATTCTT TTATATAAAA AGTTTGGTAT
2251  ACAACATGAT TTAAAAAGCA AATCAGAAAA AAGTTAGTTT TGCGTGGGGT
      TGTTGTACTA AATTTTTCGT TTAGTCTTTT TTCAATCAAA ACGCACCCCA
2301  GTGGGCATCC TGGGAATGAG AACAGACTCG CGTTTTTCTG GAGGAACTGC
      CACCCGTAGG ACCCTTACTC TTGTCTGAGC GCAAAAAGAC CTCCTTGACG
2351  GGGGATTTTT GATTAAACAA TAGTCACCGC AGAGCGGAAT TTTATGCAAC
      CCCCTAAAAA CTAATTTGTT ATCAGTGGCG TCTCGCCTTA AAATACGTTG
2401  GCTGGCTGTG CGGCACGGGG ATTTTTAATC CCCCGGCCCG TTATTCATCT
      CGACCGACAC GCCGTGCCCC TAAAAATTAG GGGGCCGGGC AATAAGTAGA
2451  CCACGGGCGA CGGGGATACA TAAACCCGAC AGCAGAGGAC GGGTGAGCGC
      GGTGCCCGCT GCCCCTATGT ATTTGGGCTG TCGTCTCCTG CCCACTCGCG
2501  GAATCCCAGA GATGATGAAA AAAGAGGCAG AGAAACGCGC CCAGGTACGT
      CTTAGGGTCT CTACTACTTT TTTCTCCGTC TCTTTGCGCG GGTCCATGCA
2551  TTTATCTTAT TGCTTTGGTG TTGTCCAGGG TGTCGGGGCT GTGCCCTGAC
      AAATAGAATA ACGAAACCAC AACAGGTCCC ACAGCCCCGA CACGGGACTG
2601  CAGGTGGCAT TTGTCTGATT GCGCGTGCGC GGTCCGACAA ATGCACATCC
      GTCCACCGTA AACAGACTAA CGCGCACGCG CCAGGCTGTT TACGTGTAGG
2651  TGCCCCGTCC TGTACGTGTT TTTTTCACCA GAACAACTTC ACGAAGTGGC
      ACGGGGCAGG ACATGCACAA AAAAGTGGT CTTGTTGAAG TGCTTCACCG
2701  GGATGAACGC TACCAACGTT GCCGGGAACG CTTCGGCGAT GATGGCATAA
      CCTACTTGCG ATGGTTGCAA CGGCCCTTGC GAAGCCGCTA CTACCGTATT
2751  CGGGCTGATA CAGGCAGCTC CCGGAGACGG ACACAGCTTG CCTGTGAGCG
      GCCCGACTAT GTCCGTCGAG GGCCTCTGCC TGTGTCGAAC GGACACTCGC
2801  GATGCCGGGA GCCGACAAGC CCGTCAGGGC GCGTCAGCGG GTTTTAGCGG
      CTACGGCCCT CGGCTGTTCG GGCAGTCCCG CGCAGTCGCC CAAAATCGCC
```

Fig. 4B

```
2851    GTGTCGGGGC GCAGCCATGA CCCAGTCACG TAGCGATAGC GGAGTGTATA
        CACAGCCCCG CGTCGGTACT GGGTCAGTGC ATCGCTATCG CCTCACATAT
2901    CTGGCTTAAT ATGTTAAATC GGAGTGGTAA TTCAGGGAAG TGCTTCATGT
        GACCGAATTA TACAATTTAG CCTCACCATT AAGTCCCTTC ACGAAGTACA
2951    GGCAAAGGAA AAATGTGGCT ATCGTGCGTA AGTGCAACAT GTAGGTAAAG
        CCGTTTCCTT TTTACACCGA TAGCACGCAT TCACGTTGTA CATCCATTTC
3001    GTGAAATGAC GCCTCCTCGC TCACTCGGTC GCTACGCTCC TGCCGTGAGA
        CACTTTACTG CGGAGGAGCG AGTGAGCCAG CGATGCGAGG ACGGCACTCT
3051    CTGCGGCGGG CGTTACCGGC TCACAAATAA CGGGATACGC AGGCAGTGCT
        GACGCCGCCC GCAATGGCCG AGTGTTTATT GCCCTATGCG TCCGTCACGA
3101    CAAATCAGGA AGGACCGGAA AAAGGATGCG GCGTAGCCGT TTTTCCATAG
        GTTTAGTCCT TCCTGGCCTT TTTCCTACGC CGCATCGGCA AAAAGGTATC
3151    GCTCCGCCCC CCTGACAAGC ATCACGAAAT CTGACGCTCA AATCAGTGGC
        CGAGGCGGGG GGACTGTTCG TAGTGCTTTA GACTGCGAGT TTAGTCACCG
3201    GGCGAAACCC GACAGGACTA TAAAGATCCC AGGCGTTTCC CCTGGTAGC
        CCGCTTTGGG CTGTCCTGAT ATTTCTAGGG TCCGCAAAGG GGACCATCG
        TCCCTCGTGC GCTCTCCTGT TCCTGCCTTT CGGTTTACCG GTGTCATTCC
        AGGGAGCACG CGAGAGGACA AGGACGGAAA GCCAAATGGC CACAGTAAGG
3301    GCTGTTATGG CCGCGTTTGT CTCATTCCAC GCCTGACACT CAGTTCCGGG
        CGACAATACC GGCGCAAACA GAGTAAGGTG CGGACTGTGA GTCAAGGCCC
3351    TAGGCAGTTC GCTCCAAGCT GGACTGTATG CACGAACCCC CCGTTCAGTC
        ATCCGTCAAG CGAGGTTCGA CCTGACATAC GTGCTTGGGG GGCAAGTCAG
3401    CGACTACCAC GCCCGTTCCG GTAACTATCA ACTTGAGTCC AACCCGGAAA
        GCTGATGGTG CGGGCAAGGC CATTGATAGT TGAACTCAGG TTGGGCCTTT
3451    GACACGACAA ATCGCCAGTG GCGGTAGCCA TTGGTAACTG AGATGTGCGA
        CTGTGCTGTT TAGCGGTCAC CGCCATCGGT AACCATTGAC TCTACACGCT
3501    GAGATTTATC TGGAGTTCTT GAAGTGGGGG CCTGAGTGCG GCTACACTGG
        CTCTAAATAG ACCTCAAGAA CTTCACCCCC GGACTCACGC CGATGTGACC
3551    AAGGACAGTT TAGGTGACTC GTCTCGCACA AGACAGTTAC CAGGTTAAGC
        TTCCTGTCAA ATCCACTGAG CAGAGCGTGT TCTGTCAATG GTCCAATTCG
3601    AGTTCCCCAA CTGACCTAAC CTTCGATCAA ACCACCTCCC CAGGTGGTTT
        TCAAGGGGTT GACTGGATTG GAAGCTAGTT TGGTGGAGGG GTCCACCAAA
3651    TTTCGTTTTC AGAGCAAGAG ATTACGCGCA GAAAAAAAGG ATCTCAAGAA
        AAAGCAAAAG TCTCGTTCTC TAATGCGCGT CTTTTTTTCC TAGAGTTCTT
3701    GATCCTTTTT ACAGGAGCGA TTATCGTCTT CATCCATGAA GGCGTTTGAA
        CTAGGAAAAA TGTCCTCGCT AATAGCAGAA GTAGGTACTT CCGCAAACTT
3751    GATTAAACCG GCCTATTTCA TAGATCGTAA AATCAGGGTT TTGGGATGGC
        CTAATTTGGC CGGATAAAGT ATCTAGCATT TTAGTCCCAA AACCCTACCG
3801    CGATGAAACC CCATAAAAAC CCATAAATAC ATACACCTAC TAACAATCAT
        GCTACTTTGG GGTATTTTTG GGTATTTATG TATGTGGATG ATTGTTAGTA
3851    CTTTTGCTGT ACCAGGGTAT GAAAAGTCTC AGGGTTCCAC CCCAGAATAC
        GAAAACGACA TGGTCCCATA CTTTTCAGAG TCCCAAGGTG GGGTCTTATG
3901    GCCATCAACA AGTCCTGTCA CACCGCCAAA TAACATGCAA AAAATTGCGG
        CGGTAGTTGT TCAGGACAGT GTGGCGGTTT ATTGTACGTT TTTTAACGCC
3951    ATGACCGTAA TCCGGGGTGC AGATCAATGA CTGAGACAAG TATAAACTTC
        TACTGGCATT AGGCCCCACG TCTAGTTACT GACTCTGTTC ATATTTGAAG
4001    ATGCAAAAAG TAATTACAAT CAGTCCCAAA GTCAGCGGTG TCCCGGCCCT
        TACGTTTTTC ATTAATGTTA GTCAGGGTTT CAGTCGCCAC AGGGCCGGGA
4051    GATAATCATG CCCGGATTAT CTGAATTTCT CAGCGGGGGC TGTGAGCGCC
        CTATTAGTAC GGGCCTAATA GACTTAAAGA GTCGCCCCCG ACACTCGCGG
4101    ACAACCTGTA TCCAAGAGCG GTGCCTACGA GCAGTCCTGC CGTCATCATT
        TGTTGGACAT AGGTTCTCGC CACGGATGCT CGTCAGGACG GCAGTAGTAA
4151    GTAAGGCTTA CGCCAGCAAG TTTTGTCTCA GTGATAACAC CTTATGCTCC
        CATTCCGAAT GCGGTCGTTC AAAACAGAGT CACTATTGTG GAATACGAGG
4201    CCATACAAGG AAAAGTATCG GGAGAAAAAA CAAACGCCCG TTGTCATCT
        GGTATGTTCC TTTTCATAGC CCTCTTTTTT GTTTGCGGGC AACAGTAGA
4251    CCCGGTCATA AAGAGCAGCA AAACCGCGTC GTAGTAAAAA AGCCAGCAGG
        GGGCCAGTAT TTCTCGTCGT TTTGGCGCAG CATCATTTTT TCGGTCGTCC
```

Fig. 4C

```
4301  ATCAAGCTTC AGGGTTGAGA TGTGTATAAG AGACAGACTC TAGCCAGTTT
      TAGTTCGAAG TCCCAACTCT ACACATATTC TCTGTCTGAG ATCGGTCAAA
4351  CCAAGTAGAA ACTACAGTTT CTAAACTGCA ACTTTTTCTA CTTTTTGCAA
      GGTTCATCTT TGATGTCAAA GATTTGACGT TGAAAAAGAT GAAAAACGTT
4401  CTTAATCTAT TGACTAGTCC TTTATAAATG TTAAAACATA TATATAGAAA
      GAATTAGATA ACTGATCAGG AAATATTTAC AATTTTGTAT ATATATCTTT
                                         MetGlnIle PheValLys ThrLeuThrGly·
4451  TAAATAAAAA GAGGAGGTTC ATATGCAAAT TTTTGTTAAA ACTTTAACTG
      ATTTATTTTT CTCCTCCAAG TATACGTTTA AAAACAATTT TGAAATTGAC
      ·GlyLysThrIle ThrLeuGlu ValGluSerSer AspThrIle AspAsnVal
4501  GTAAAACCAT TACCTTAGAA GTTGAATCTT CAGATACCAT TGATAATGTT
      CATTTTGGTA ATGGAATCTT CAACTTAGAA GTCTATGGTA ACTATTACAA
         LysSerLysIle GlnAspLys GluGlyIle ProProAspGln GlnAlaLeu·
4551  AAATCTAAAA TTCAAGATAA AGAAGGTATT CCTCCAGATC AACAAGCTCT
      TTTAGATTTT AAGTTCTATT TCTTCCATAA GGAGGTCTAG TTGTTCGAGA
      ·IlePheAla GlyLysGlnLeu GluAspGly AlaThrLeu SerAspTyrAsn·
4601  AATATTTGCA GGTAAACAGT TAGAAGATGG TGCTACCCTG TCTGATTATA
      TTATAAACGT CCATTTGTCA ATCTTCTACC ACGATGGGAC AGACTAATAT
          ·AIleGlnLys GluSerThr LeuHisLeuVal LeuAlaLeu AlaGlyGly
4651  ACATTCAGAA AGAATCTACC TTACATCTGG TCTTAGCTCT CGCTGGTGGT
      TGTAAGTCTT TCTTAGATGG AATGTAGACC AGAATCGAGA GCGACCACCA
         ArgPheValAsn GlnHisLeu CysGlySer HisLeuValGlu AlaLeuTyr·
4701  CGTTTTGTCA ACCAGCACCT GTGTGGTTCT CACCTGGTTG AAGCACTGTA
      GCAAAACAGT TGGTCGTGGA CACACCAAGA GTGGACCAAC TTCGTGACAT
         ·LeuValCys GlyGluArgGly PhePheTyr ThrProLys ThrLysArgGly·
4751  CCTGGTATGT GGCGAACGTG GTTTCTTCTA CACTCCTAAA ACAAAGCGCG
      GGACCATACA CCGCTTGCAC CAAAGAAGAT GTGAGGATTT TGTTTCGCGC
          ·GIleValGlu GlnCysCys ThrSerIleCys SerLeuTyr GlnLeuGlu
4801  GCATCGTTGA ACAGTGCTGT ACCTCTATCT GTTCCCTGTA CCAACTGGAG
      CGTAGCAACT TGTCACGACA TGGAGATAGA CAAGGGACAT GGTTGACCTC
          AsnTyrCysAsn Ser***
4851  AACTACTGCA ATTCTTAAGT CGACTCTAGC TACAGCCTCC TTTCGGAGGC
      TTGATGACGT TAAGAATTCA GCTGAGATCG ATGTCGGAGG AAAGCCTCCG
4901  TGTTTTTTAT C
      ACAAAAAATA G
```

Fig. 4D

INSULIN ANALOGUES OF PROLONGED ACTIVITY

The subjects of the invention are new biosynthetic analogues of recombined human insulin of prolonged therapeutic activity, which may find use in prophylaxis and treatment of diabetes mellitus.

Insulin and its various derivatives are used in large amounts in treatments of diabetes mellitus and are often manufactured on a large industrial scale. While there are many different known modified derivatives of insulin and many pharmaceutical preparations of diverse activity profiles, a drug is still sought, which would enable to maintain a constant level of glucose in a human organism for an extended period of time.

To achieve the effect of delayed and/or prolonged activity some preparations of normal human insulin contain specific additions, e.g. various amounts of protamin, a protein that forms an insoluble complex with insulin which forms deposits in subcutaneous tissues, and from which insulin is gradually released.

There are known various human insulin derivatives used in treatment of diabetes, which contain additional amino acids or have modified sequence of some amino acids. Changes of primary structure of insulin influence its secondary and tertiary structure, which affects protein's chemical and biological properties, and that in turn results in pharmacokinetic and pharmacodynamic effects. These changes are of different character, can lead to accelerated or delayed and prolonged activity of modified insulin. Active form of insulin is a monomer, which easily filters into blood after subcutaneous injection. It is known, that exogenous human insulin in solutions has hexameric form, which after application dissociates to dimers and subsequently to monomers before filtering into blood stream. One of insulin derivatives characterised by accelerated activity is lispro-insulin (Humalog®), in which the sequence of proline (28)-lysine (29) in chain B has been inverted. It makes difficult, from the sterical point, to form dimers of insulin in a solution. Second such a derivative is insulin in which proline in the position 28 of chain B has been replaced with aspartic acid. Such introduced negative charge lowers possibility of self-association of insulin monomers. Both these insulin derivatives are absorbed faster due to their structure.

Prolonged-activity recombined human insulin analogues are constructed by elongating chain B with alkaline amino acids or acylating E-amino group in lysine in chain B with aliphatic acid of about a dozen carbon atoms.

Introduction of these extra alkaline amino acids changes some chemical or physical properties of insulin. The most important change is a shift of isoelectric point in respect to unmodified natural insulin from 5.4 to the range of about 5.5 to about 8.5, which results from introduction of superfluous positive charges into the molecule. In consequence solubility of these analogues in neutral water environment is reduced, and therefore necessity of using slightly acidic environment for production of pharmaceutical preparations containing such modified insulin.

However, beside obvious advantages resulting from introduction of extra alkaline amino acids there is observed also disadvantageous reduction of stability of new analogues, stemming primarily from deamination of asparagine in position A21 occurring in acidic environment.

This issue is addressed by replacement of A21Asn with other amino acid, such as aspartic acid, glycine, alanine, threonine and others. One of such analogues is recombinant human insulin derivative in which in chain A asparagine(21) has been replaced with glycine(21) and to the C terminus of chain B have been attached two arginine residues. This is so-called glargine derivative of insulin, manufactured under the name Lantus (patent U.S. Pat. No. 5,656,722).

In the course of our research it has been established, that a human insulin derivative, where to the C terminus of chain B have been attached residues of lysine (B31 Lys) and arginine (B32Arg) shows biological activity that is similar to glargine derivative, which is already present on the market. Preliminary research performed on animals indicates, that this preparation, called lizarginsulin, is characterised by prolonged activity and a flat release profile mimicking secretion of natural insulin, and from a clinical point of view—reduction of nocturnal hypoglycaemias. Because of exceptional similarity to human insulin and also to proinsulin, there could be expected good research results, enabling gradual development of the drug candidate and its final commercialisation. It is crucial, that LysArg sequence at C terminus of chain B of human insulin is found in human proinsulin, and one should expect transformation of lizarginsulin into human insulin by present carboxypeptidase C. This means, that first metabolite of lizarginsulin in human organism can be human insulin of well known and acceptable characteristics, even in the case of exogenous hormone. There was performed extended preclinical research on rats, which confirmed prolonged activity of the new insulin analogue.

However it came out that this derivative apart of its advantageous biological activity is characterised by insufficient stability in acidic injection solutions. The main cause of insufficient stability, which manifests itself primarily as deamidation, is presence of asparagine residue at C terminus of chain A, where in acidic water environment can occur a deamidation autocatalysed by a proton from carboxyl group.

Therefore the aim of this invention is providing new analogues of insulin, which would be characterised by an adequate stability in acidic injection solutions (pH 3.5-5), and at the same time would possess the required biological activity. It is especially desirable that they would show characteristics of biological activity of natural insulin. It is also particularly important, that the start of activity of the new derivatives was practically immediate, just after administration to the patient, with the ability of prolonged release of a part of the dose. This would enable to provide both accelerated and prolonged activity of the pharmaceutical preparation containing insulin analogues.

The above stated goal was unexpectedly achieved in this invention.

The basic aspect of the invention is an insulin derivative or its pharmaceutically acceptable salt containing two polypeptides constituting chain A and chain B, where amino acid sequence of chain A has been chosen from SEQ ID No 1-5, while amino acid sequence of chain B has been chosen from SEQ ID No 6-8. Preferred insulin derivative or its pharmaceutically acceptable salt according to the invention is characterised by being an analogue of recombined human insulin of isoelectric point 5-8.5 and formula 1:

Formula 1

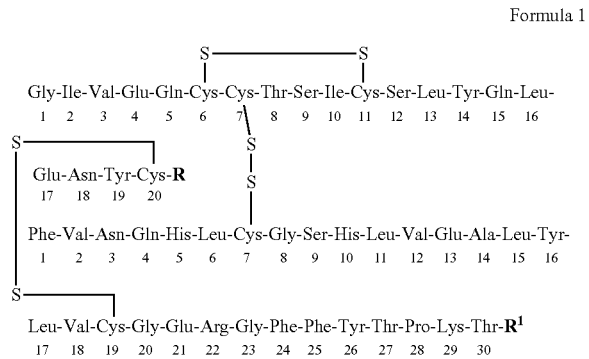

where R denotes an $NH_2$ group or a group according to formula Asn-$R^2$, where $R^2$ denotes a neutral L-amino acid or an $NH_2$ group;
and R1 denotes B31Lys-B32Arg or B31Arg-B32Arg or B31Arg, where B3Asn may be alternatively replaced by other amino acid, advantageously by Glu.
Advantageously, the insulin derivative or its physiologically acceptable salt according to the invention is characterised by this, that:
R in the formula 1 denotes group of formula Asn-$R^2$, wherein $R^2$ denotes Gly and $R^1$ denotes B31 Lys-B32Arg, or
R in the formula 1 denotes group of formula Asn-$R^2$, wherein $R^2$ denotes Ala and $R^1$ denotes B31 Lys-B32Arg or
R in the formula 1 denotes group of formula Asn-$R^2$, wherein $R^2$ denotes Ser and $R^1$ denotes B31 Lys-B32Arg, or
R in the formula 1 denotes group of formula Asn-$R^2$, wherein $R^2$ denotes Thr and $R^1$ denotes B31 Lys-B32Arg, or
R in the formula 1 denotes group of formula Asn-$R^2$, wherein $R^2$ denotes group $NH_2$ and $R^1$ denotes B31 Lys-B32Arg, or
R in the formula 1 denotes group $NH_2$ and $R^1$ denotes B31 Lys-B32Arg, or
R in the formula 1 denotes group of formula Asn-$R^2$, wherein $R^2$ denotes Gly a $R^1$ denotes B31Arg-B32Arg, or
R in the formula 1 denotes group of formula Asn-$R^2$, wherein $R^2$ denotes Ala a $R^1$ denotes B31Arg-B32Arg, or
R in the formula 1 denotes group of formula Asn-$R^2$, wherein $R^2$ denotes Thr a $R^1$ denotes B31Arg-B32Arg, or
R in the formula 1 denotes group of formula Asn-$R^2$, wherein $R^2$ denotes Ser a $R^1$ denotes B31Arg-B32Arg, or
R in the formula 1 denotes group of formula Asn-$R^2$, wherein $R^2$ denotes group $NH_2$ and $R^1$ denotes B31Arg-B32Arg, or
R in the formula 1 denotes group $NH_2$ a $R^1$ denotes B31Arg-B32Arg, or
R in the formula 1 denotes group of formula Asn-$R^2$, wherein $R^2$ denotes Gly a $R^1$ denotes B31Arg, or
R in the formula 1 denotes group of formula Asn-$R^2$, wherein $R^2$ denotes Ala a $R^1$ denotes B31Arg, or
R in the formula 1 denotes group of formula Asn-$R^2$, wherein $R^2$ denotes Thr a $R^1$ denotes B31Arg, or
R in the formula 1 denotes group of formula Asn-$R^2$, wherein $R^2$ denotes Ser a $R^1$ denotes B31Arg, or
R in the formula 1 denotes group of formula Asn-$R^2$, wherein $R^2$ denotes group $NH_2$ and $R^1$ denotes B31Arg, or
R in the formula 1 denotes group $NH_2$ a $R^1$ denotes B31Arg, or
R in the formula 1 denotes group of formula Asn-$R^2$, wherein $R^2$ denotes Gly, $R^1$ denotes B31 Lys-B32Arg, and B3Asn has been replaced with B3Glu.

As described before, in the case of glargin the problem of low stability has been solved by replacing asparagine in the position A21 with glycine. Research, which aimed at obtaining an insulin analogue exhibiting prolonged activity and stability in acidic injection solutions as described in the invention, went in different direction. In order to block carboxyl group responsible for low stability, there were obtained new derivatives of lizarginsulin with carboxyl group in asparagine residue modified in different ways, using methods of genetic engineering and enzymatic transformation. As a result of the conducted research it unexpectedly turned out, that chemical and biological properties, similar to these of glargine and lizargine derivative, are exhibited by derivatives of human insulin of formula 1, where chain A has been elongated at C terminus with a residuum of neutral amino acid (A22) or where carboxyl group of asparagine or cysteine at C terminus of chain A has been transformed into carboxyamid group, and to the C terminus of chain B there were attached residues of lysine and arginine (B31Lys-B32Arg), or two arginine residues (B31Arg-B32Arg), or one arginine residue (B31Arg). New analogues obtained in such a way are characterised by proper stability in acidic injection solutions (pH 3.5-5) and at the same time exhibit desired biological activity.

Introduced modification unexpectedly led to obtaining stable pharmaceutical compositions of insulin derivatives, at the same time preserving biological activity and causing a shift of isoelectric point to pH between 5 and 8, therefore reducing solubility of the new insulin derivative in physiological pH at the place of injection. This causes precipitation of insulin derivative microdeposit in subcutaneous tissue and subsequently slow release of the substance to the blood, which causes maintaining of theraupetical level by a prolonged time.

Properties of these compounds and their compositions have been confirmed by stability research and by researching their activity in animals with experimental diabetes. During these there was unexpectedly found remarkably prolonged effect of hypoglycaemic activity, which lasted also for a long time after stopping administration of the medicine, in contrast to what was observed for a reference commercially available insulin derivative of prolonged activity. This allows supposing, that properties of derivatives, which are the subject of the invention, will enable significantly less frequent administration of the medicine, which will increase effectiveness, safety and comfort of the patients therapy. It is also important, that start of activity of the new derivatives according to the invention is practically immediate, which means that these compounds unexpectedly exhibit characteristics of biological activity of known insulin analogues of both accelerated and prolonged activity.

Examples of insulin derivatives of formula 1 are such as, but not limited to, these exhibited below.

| A22Gly | -human insulin- | B31LysB32Arg | (insulin GKR) |
|---|---|---|---|
| A22Ala | -human insulin- | B31LysB32Arg | (insulin AKR) |
| A22Ser | -human insulin- | B31LysB32Arg | (insulin SKR) |
| A22Thr | -human insulin- | B31LysB32Arg | (insulin TKR) |
| de(A21Asn)A20Cys-$NH_2$ | -human insulin- | B31LysB32Arg | (insulin XKR) |

-continued

| | | | |
|---|---|---|---|
| A21Asn-NH$_2$ | -human insulin- | B31LysB32Arg | (insulin ZKR) |
| A22Gly | -human insulin- | B3GluB31LysB32Arg | (insulin GEKR) |
| A22Gly | -human insulin- | B31ArgB32Arg | (insulin GRR) |
| A22Ala | -human insulin- | B31ArgB32Arg | (insulin ARR) |
| A22Ser | -human insulin- | B31ArgB32Arg | (insulin SRR) |
| A22Thr | -human insulin- | B31ArgB32Arg | (insulin TRR) |
| de(A21Asn)A20Cys-NH$_2$ | -human insulin- | B31ArgB32Arg | (insulin XRR) |
| A21Asn-NH$_2$ | -human insulin- | B31ArgB32Arg | (insulin ZRR) |
| A22Gly | -human insulin- | B31Arg | (insulin GR) |
| A22Ala | -human insulin- | B31Arg | (insulin AR) |
| A22Ser | -human insulin- | B31Arg | (insulin SR) |
| A22Thr | -human insulin- | B31Arg | (insulin TR) |
| de(A21Asn)A20Cys-NH$_2$ | -human insulin- | B31Arg | (insulin XR) |
| A21Asn-NH$_2$ | -human insulin- | B31Arg | (insulin ZR) |

To simplify names of recombined human insulin analogues, which are the subject of the invention, they were assigned symbols which are composed of the name "insulin" and 2-4 capital letters of alphabet, which denote amino acid residues, which were added or which replaced these present in the parent particle of human insulin. In the most cases these letters are consistent with one-letter amino acid residues code recognised in the literature. Only for two residues, that do not occur naturally, there were used additional letters, namely "Z" and "X". In both cases the letter denotes a residue placed at C terminus of chain A, which where instead of the terminal COOH group there's CONH$_2$ group; letter "Z" denotes corresponding asparagine amide (that is A21Asn-NH$_2$), and letter "X"—cysteine amide (that is de(A21 Asn)A20Cys-NH$_2$).

Insulin analogues of formula 1 were produced by a series of genetic manipulations using standard methods of genetic engineering.

To this end there were constructed modifications of the gene encoding recombined human proinsulin using genetic techniques such as for example site specific mutagenesis. Site-specific mutagenesis reaction has been performed using Stratagene kit (cat. no. 200518-5), as a template has been used plasmid DNA plGALZUINS—p5/ZUINS or plGTET-ZUINS—p6/ZUINS. Also any other DNA containing proper sequence encoding recombined human proinsulin or preproinsulin can be used as the template.

According to the invention, in the light of recognised terminology, recombined human proinsulin is understood as a polypeptide chain where chains A and B of human insulin are connected by dipeptide Lys-Arg or Arg-Arg, and the recombined preproinsulin—a combination of proinsulin and an additional leader polypeptide, for example ubiquitin, or SOD or their fragments.

Reaction mixture was used to transform competent cells of a proper *Escherichia coli* strain, as for example DH5α, DH5, or HB101, however it is possible to use cells of other *E. coli* strains or cells of other microorganisms, or other known cell lines which can be used for expression of recombined proteins. Plasmid containing given modification of a gene encoding recombined human proinsulin was isolated and sequenced in order to verify correctness of nucleotide sequence. According to the variant of the invention, plasmid with the modified gene encoding recombined human proinsulin was used to transform competent *E. coli* DH5α cells and bacteria were cultured in LB media with addition of selection antibiotic (0.01 mg/ml) in the volume of 500 ml, at temp. 37° C., 200 rpm for 18 h. Bacterial material was prepared for strain bank, samples in proportion 1:1 of bacteria culture and 40% glycerol were deposited at −70° C.

Variants of recombined preproinsulin obtained by expression in *E. coli* strains were isolated in the form of inclusion bodies, after the cells had been disintegrated, and subsequently were subjected to standard processes of fusion proteins purification. Solution of hybrid protein with insulin analog obtained after renaturation was subjected to controlled treatment with tripsine, analogously to case of many methods known beforehand and described e.g. by Kemmlera et al. in J. Biol. Chem., Vol. 246, page 6786-6791 (1971) or patents U.S. Pat. No. 6,686,177 and U.S. Pat. No. 6,100,376. Obtained insulin analogues were subjected to the process of purification using known methods, mainly low-pressure chromatography, ultrafiltration and/or HPLC. The product was precipitated from sufficiently purified solution of insulin analogue.

In order to obtain derivatives containing at the C terminus of chain A residue A21 Asn-NH$_2$ or A20Cys-NH$_2$, there were used a-amidating enzymes (α-AE), catalysing conversion of naturally appearing in living organisms prohormones, which are reaction substrates converted into active a-amid forms.

Enzyme PAM (peptidylglycine a-amidating monooxygenase) is a protease with dual activity, denoted as activity PHM (Peptidylglycine alpha-hydroxylating monooxygenase) and PAL (peptidylamidoglycolate lyase activity) (Diagram 1), which enables obtaining C terminal amide. It was investigated, that half of peptide hormones, such as oxytocin or vasopressin require achieving their optimal activity a C-terminal amid group. In this reaction the amid group originates from C-terminal gycine residue, which is here direct reaction precursor (Satani M., Takahashi K., Sakamoto H., Harada S., Kaida Y., Noguchi M.; Expression and characterization of human bifunctional peptidylglycine alpha-amidating monooxygenase. *Protein Expr Purif.* 2003 Apr; 28(2):293-302.; Miller D. A., Sayad K. U., Kulathila R., Beaudry G. A., Merkler D. J., Bertelsen A. H.; Characterization of a bifunctional peptidylglycine alpha-amidating enzyme expressed in Chinese hamster ovary cells. *Arch Biochem Biophys.* 1992 Nov. 1; 298(2):380-8).

glycine-extended precursor

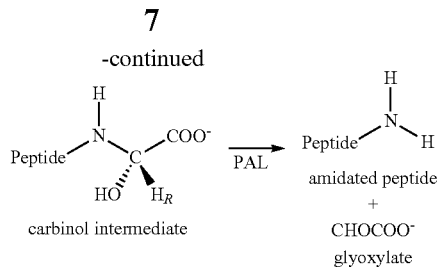

Precursor with Gly hydroxyl derivative glyoxylate Diagram 1 Outline of α-amidation of a peptide by active PAM protease (according to Satani M., Takahashi K., Sakamoto H., Harada S., Kaida Y., Noguchi M.; Expression and characterization of human bifunctional peptidylglycine alpha-amidating monooxygenase. *Protein Expr Purif.* 2003 Apr; 28(2): 293-302.). PAM protease is a protein which is found inter alia in eukaryotic organisms of different length of amino acid chain. In this project there was used a protease originating from human organism (Homo sapiens), in which there are found 6 genes encoding proteins exhibiting activity of a-amidating protease.

The basic physicochemical property of recombined human insulin analogues of formula 1, which differentiates them from human insulin, is their value of isoelectric point, which has values from about 5 to about 8. This means good solubility of the compounds in solutions of acidic to slightly acidic pH. This property enabled preparation of composition—solutions of new insulin derivatives in acidic pH.

An aspect of the invention is also pharmaceutical composition characterised by this, that it contains effectively acting amount of insulin derivative according to the invention or its pharmaceutically acceptable salt, which are defined above. Favourably, the pharmaceutical composition according to the invention contains also from 10 to 50 µg/ml of zinc.

Consecutive aspect of the invention is also use of insulin derivative according to the invention or its pharmaceutically acceptable salt, which were defined above, to manufacture drug for treatment or prevention of diabetes.

In accordance with the above, the pharmaceutical composition, according to the invention, contains effectively acting amount of biosynthetic analogue of human insulin of formula 1 or its pharmacologically acceptable salt and auxiliary substances.

A salt of biosynthetic human insulin analogue according to the invention can be for example a salt of alkaline metal or ammonium salt.

Intended for administration composition according to the invention is prepared in the form of solution and contains: effectively acting amount of biosynthetic analogue of human insulin of formula 1 or its pharmacologically acceptable salt and auxiliary substances, such as: isotonic agents, preservatives agents, stabilizing agents, optionally buffering agents.

Amount of the active substance used in the composition according to the invention is about 1-1600, favourably 10-1200, especially favourably 10-500 u/ml. In case of each human insulin analogue, which is subject of this invention, by 1 unit (1 u) is meant 1 auxiliary unit, containing the same number of moles of the analogue as 1 international unit of insulin, corresponding to 6 nMol (that is $6 \times 10^{-9}$ Mol).

For pharmaceutical composition according to the invention pH value of the solution is from about 3.5 to about 5, favourably 4.0-4.5.

Generally, auxiliary substances in compositions according to the invention are the same substances that are used in preparations containing known recombined human insulin.

Isotonic substance according to the invention can be any substance, which allows obtaining solution isoosmotic in respect to human blood plasma. To typical isotonic agents used in pharmacy belong such substances as sodium chloride, mannitol, glycine, preferably glycerine. Favourable is use of glycerine.

Useful conserving agents to be used in composition according to the invention are compounds chosen from the group to which belongs m-cresole, phenol or their mixtures.

New derivatives, similarly to recombined normal human insulin, are stabilised by addition of zinc ions, introduced into the solution in the form of, among other, zinc chloride or oxide. Amount of the zinc can range from around 5 µg/ml to around 150 µg/ml.

A following example of a content of the composition containing derivatives of recombined human insulin according to the invention has been developed: 10-500 u/ml of biosynthetic analogue of human insulin of formula 1 or its pharmacologically acceptable salt, 16 mg/ml of glycerine, 2.7-3 mg/ml m-cresole, 10-50 µg/ml of zinc and water for injection to 1 ml.

To better explain the essence of the invention this description has been extended with a detailed discussion of examples of the invention's realisation, which encompasses also enclosed list of sequences and figures, of which:

FIG. 1 presents structure of plasmid p5/ZUINSGly(22A) containing a gene encoding GKR protein of recombined insulin.

FIG. 2 presents nucleotide and amino acid sequence of plasmid p5/ZUINSGly(22A).

FIG. 3 presents structure of plasmid p6/ZUINSSer(22A) containing a gene encoding insulin SKR protein.

FIG. 4 presents nucleotide and amino acid sequence of plasmid p6/ZUINSSer(22A).

Figure 5:
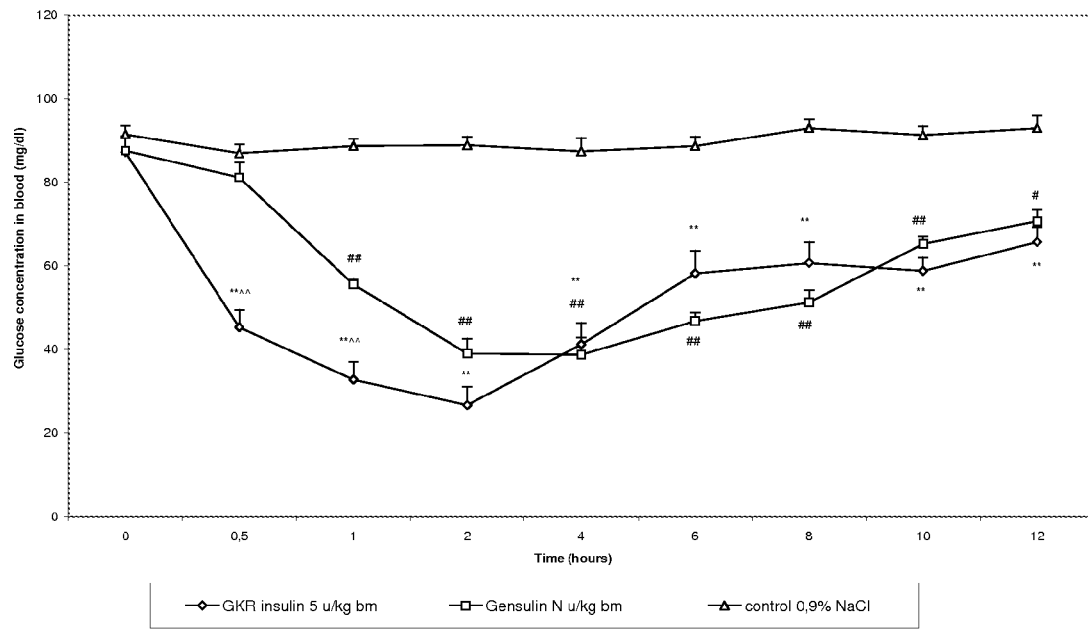

FIG. 5 presents influence of single dose administration of GKR insulin (in the dose of 5 u/kg of body mass on glucose concentration in blood of normoglycaemic rats, compared with preparation of Gensulin N. Average values±SEM. Statistical significance **p<0.01: Insulin GKR vs. initial glucose concentration; ##p<0.01, #p<0.05: Gensulin N vs. initial glucose concentration; ˆˆp<0.01: Insulin GKR vs. Gensulin N.

Figure 6:
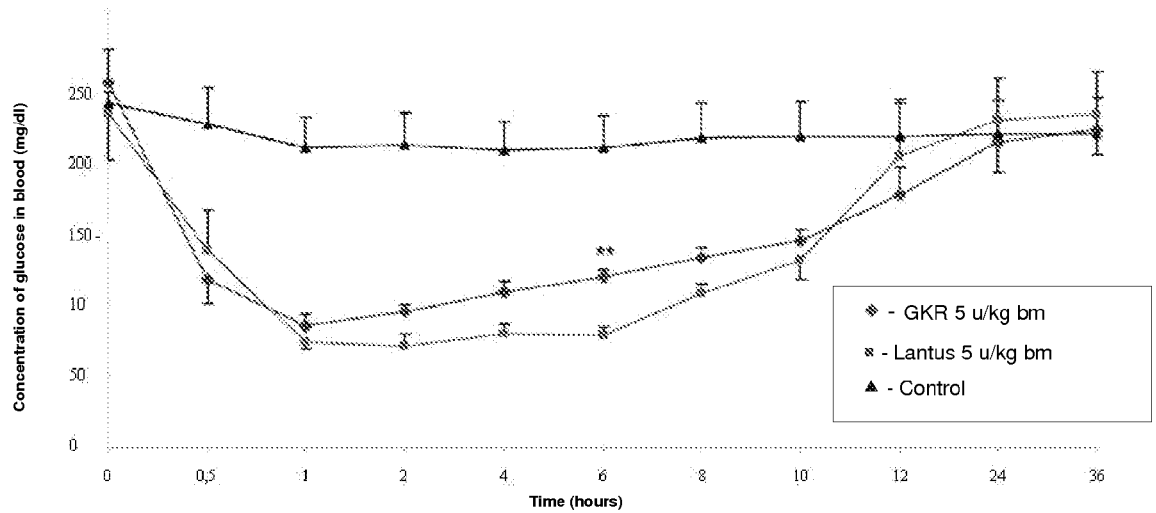
Figure 7:
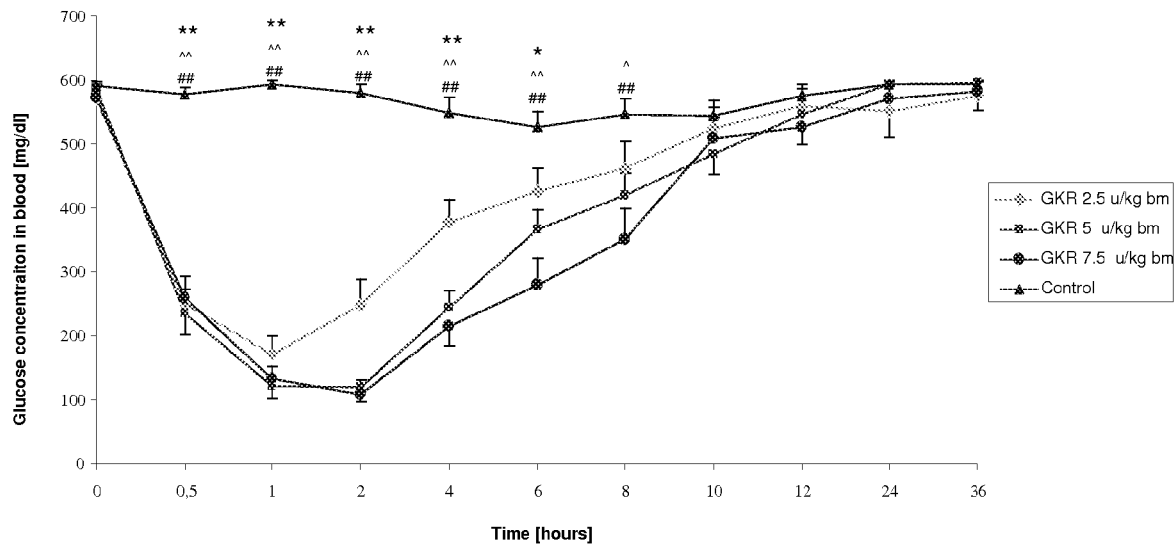
Figure 8:
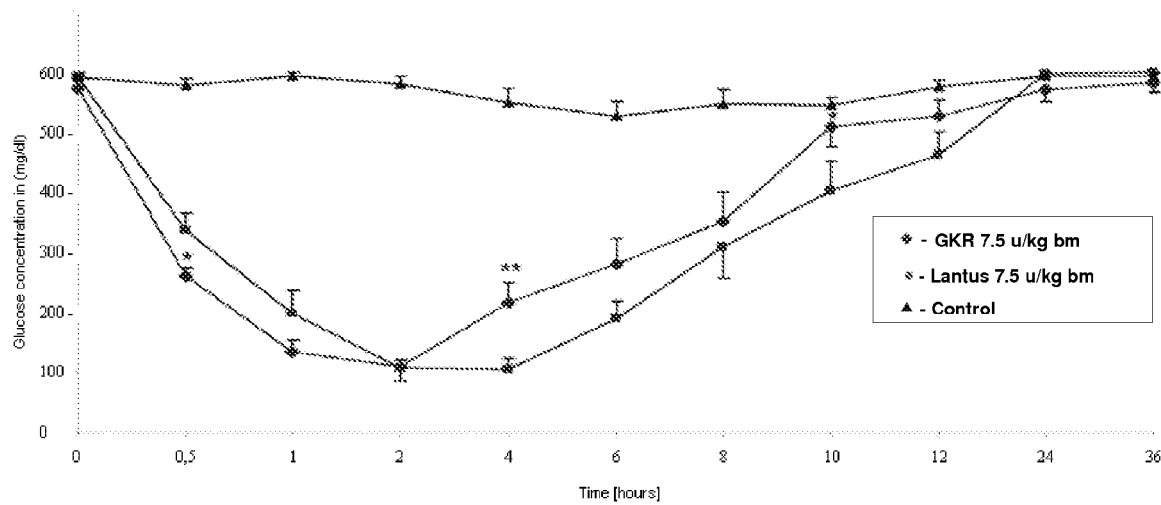
Figure 9:
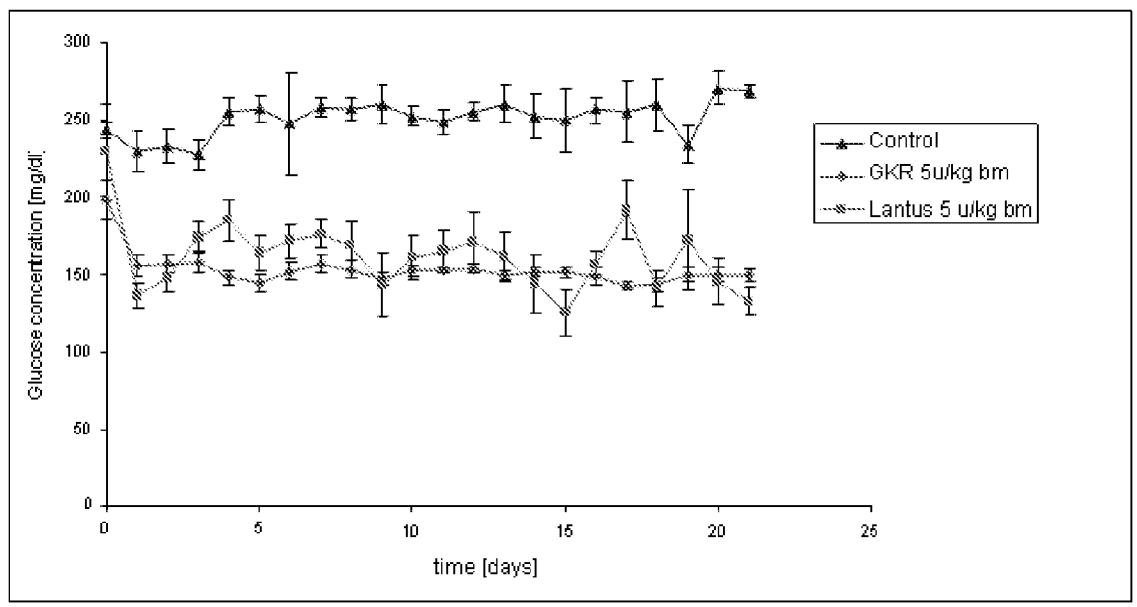

FIG. 6 presents influence of single dose administration of GKR insulin (in dose of 5 u per kg of body mass) on glucose concentration in blood of rats with mild streptozotocin-induced diabetes (in comparison with Lantus preparation). 0—fixed hyperglycaemia; control—physiological salt solution 10 µl /200 g bm. Statistical significance: **p<0.01*p<0.05 GKR vs. Lantus;

FIG. 7 presents influence of single dose administration of GKR insulin (in doses of 2.5 u, 5u and 7.5 u per kg of body mass) on glucose concentration in blood of rats with severe streptozotocin-induced diabetes. 0—fixed hyperglycaemia; control—physiological salt solution 10 µl/200 g bm. Statistical significance: **p<0.01*p<0.05 GKR 2.5 u vs control; ˆˆp<0.01 ˆp<0.05 GKR 5 u vs control; ##p<0.01 #p<0.05 GKR 7.5 u vs control FIG. 8 presents influence of single dose administration of GKR insulin (in dose of 7.5 u per kg of body mass) on glucose concentration in blood of rats with severe streptozotocin-induced diabetes (in comparison with Lantus preparation). 0—fixed hyperglycaemia; control—physiological salt solution 10 µl/200 g bm. Statistical significance: **p<0.01, *p<0.05 GKR vs. Lantus;

FIG. 9 presents glucose concentration in blood of rats after multiple administrations of GKR insulin in doses of 5 u per kg of body mass in a model of mild streptozotocin-induced diabetes (in comparison with Lantus preparation); 0—fixed hyperglycaemia; control—physiological salt solution 10 μl/200 g bm.

Figure 10:
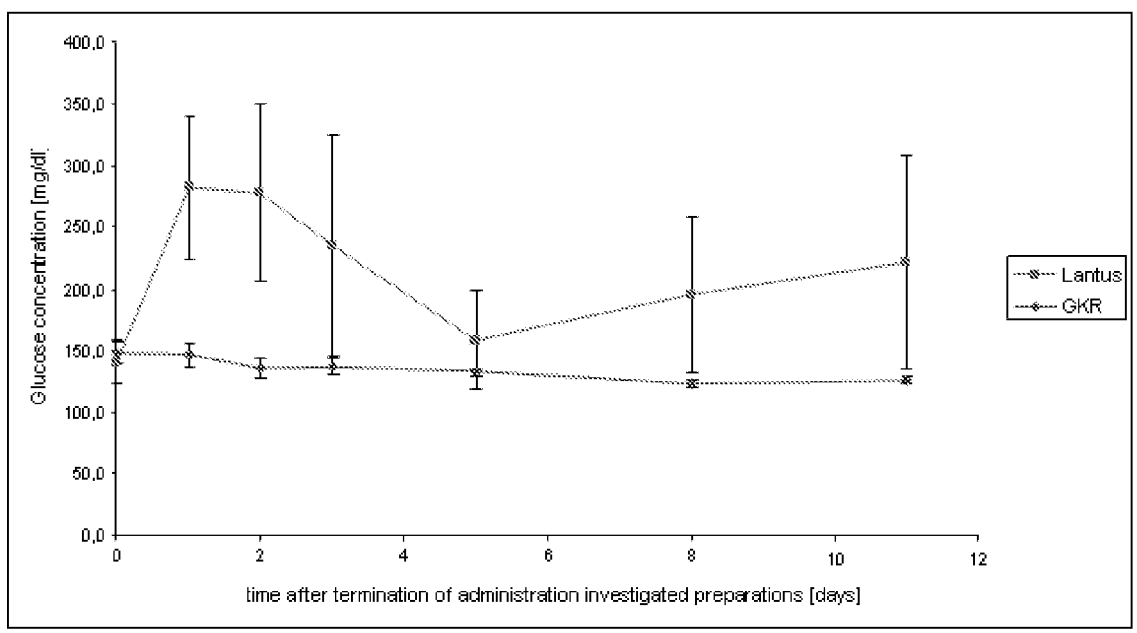
Figure 11:
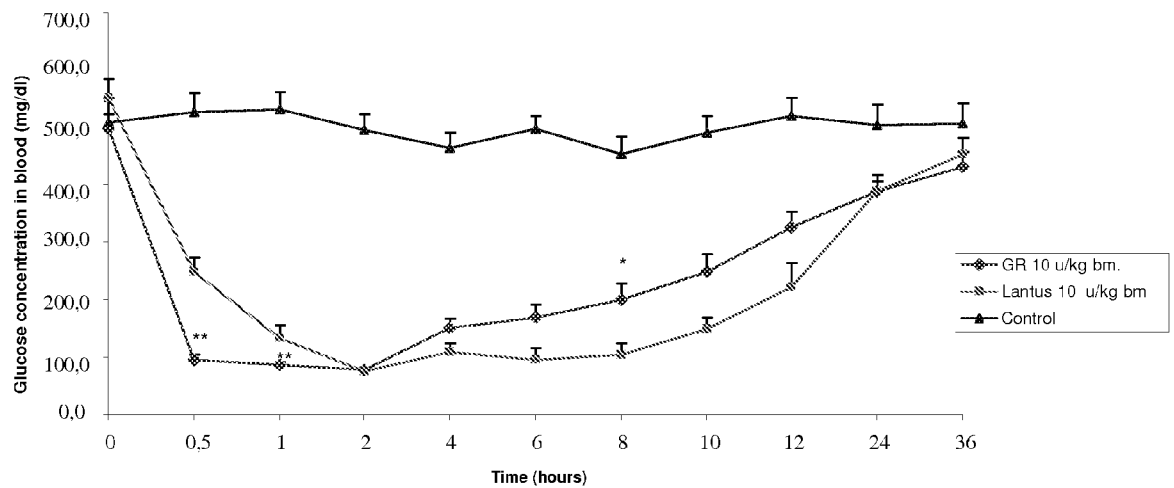
Figure 12:
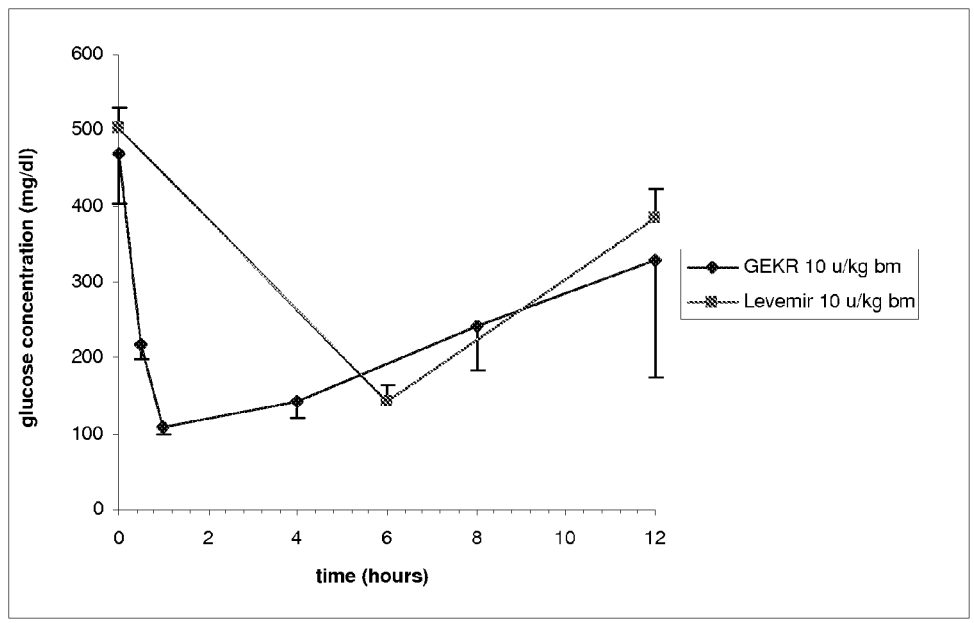

FIG. 10 presents glucose concentration in blood of rats in the period after stopping administration of GKR insulin in dose of 5 u per kg of body mass in a model of mild streptozotocin-induced diabetes (in comparison with Lantus preparation);

FIG. 11 presents influence of single dose administration of GR insulin (in doses of 10 u per kg of body mass) on glucose concentration in blood of rats with moderate streptozotocin-induced diabetes compared with Lantus preparation. 0—fixed hyperglycaemia; control—physiological salt 10 μl/200 g bm. 0—fixed hyperglycaemia; control—physiological salt solution 10 μl/200 g bm. Statistical significance: **p<0.01, *p<0.05 GR vs. Lantus;

FIG. 12 presents influence of single dose administration of GEKR insulin (in dose of 10 u per kg of body mass) on glucose concentration in blood of rats with moderate streptozotocin-induced diabetes compared with Levemir preparation. 0—fixed hyperglycaemia;

EXAMPLE 1

Construction of p5/ZUINSGly(22A) Plasmid and Obtaining of a Strain Transformed with this Plasmid.

To construct a gene encoding recombined INSGly(22A) proinsulin there was used p5/ZUINS plasmid, in which a DNA fragment encoding recombined insulin precursor is added to a modified gene of synthetic ubiquitin. In the ubiquitin gene arginine codons have been replaced with alanine codons and to the C terminus of ubiquitin gene there has been added aditional arginine codon. Peptide which constitutes part of ubiquitin is a carrier for insulin precursor, and is a condition for high efficiency of fusion protein synthesis in *E. coli*. The region encoding the modified fusion protein ubiquitin-human insulin is placed under control of pms (WO05066344 A2) promoter. The plasmid carries ampicillin resistance gene. For construction of p5/ZUINS vector there was used pIGAL1 plasmid, whose sequence deposited in Gene Bank has number AY424310.

The recombined INSGly(22A) proinsulin gene differs from the model human proinsulin gene in such a way, that it has attached additional GGT codon at C terminus of chain A. In result amino acid sequence of chain A is being elongated at position 22 with Gly-lycine-amino acid residue.

In order to modify the gene encoding human recombined proinsulin sequence by adding of GGT (Gly) codon at its C terminus, there were designed following primers for point mutagenesis reaction:

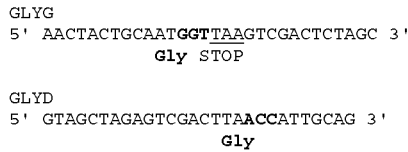

The point mutagenesis reaction was carried out using Stratagene kit (catalogue no 200518-5). As the template there has been used plasmid DNA p5/ZUINS. *Escherichia coli* DH5 a competent cells were transformed with reaction mixture. Plasmid p5/ZUINSGly(22A) has been isolated and sequenced in order to verify presence of GGT nucleotides encoding glycine and the validity of plasmid sequence. Plasmid with the modified gene encoding recombined p5/ZUINSGly(22A) proinsulin has been used in transformation of competent *E. coli* DH5α cells which were subsequently cultivated for 18 hours in LB medium with addition of ampicillin (0.01 mg/ml) in the volume of 500 ml, at 37° C., 200 rpm. Bacteria material has been prepared for strain bank, samples containing 1:1 bacterial cultures and 40% glycerol have been deposited at −70° C.

Obtained *Escherichia coli* strain constitutes the initial biological material in the process of obtaining GKR insulin via biosynthesis, according to Example 10.

Genetic construction of p5/ZUINSGly(22A) plasmid
Plasmid p5/ZUINSGly(22A) is 4775 base pairs long and is built of following regulatory sequences and genes:
- from 374 by to 1234 by there is ampicillin resistance gene AMP R,
- from 4158 by to 4323 by there is a region encoding pms promoter,
- from 4327 by to 4554 by there is a sequence encoding modified synthetic ubiquitin gene ZUBI,
- from 4558 by to 4722 by there is a sequence encoding the recombined INSGly(22A) proinsulin gene,
- from 4729 by to 4775 by there is a region encoding transcription terminator Ter. Structure of p5/ZUINSGly (22A) plasmid containing the gene encoding recombined human insulin protein (GKR insulin) is shown schematically in FIG. 1, and its nucleotide and amino acid sequence at FIG. 2.

EXAMPLE 2

Construction of p5/ZUINSGly(22A)Arg(31 B) Plasmid and Obtaining a Strain Transformed with it.

In construction of recombined INSGly(22A)Arg(31 B) proinsulin gene there was used p5/ZUINSGly(22A) plasmid. The recombined INSGly(22A)Arg(31 B) gene is characterised by replacement of AAG (Lys) codon with CGT (Arg) codon at position 31 of chain B.

In order to modify the gene encoding sequence of recombined INSGly(22A) proinsulin there were designed following primers for point mutagenesis reaction:

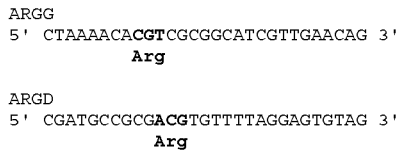

Stratagene kit (cat. no 200518-5) has been used to conduct point mutagenesis reaction. Isolation, verification of validity of plasmid nucleotide sequence and obtaining *E. coli* DH5α bacteria with p5/ZUINSGly(22A)Arg(31 B) plasmid have been performed as in Example 1. Obtained *Escherichia coli* strain is the initial biological material in the process of manufacturing GR insulin via the biosynthesis according the Example 11.

EXAMPLE 3

Construction of p5/ZUINSSer(22A)Arg(31B) Plasmid and Obtaining of a Strain Transformed with it To construct a gene of recombined INSSer(22A)Arg(31 B) proinsulin there was used p5/ZUINSGly(22A)Arg(31B)

plasmid. The difference between the gene encoding recombined INSSer(22A)Arg(31B) proinsulin and the gene encoding recombined proinsulin INSGly(22A)Arg(31 B) is a replacement of GGT (Gly) codon with TCT (Ser) codon at position 22 of chain A.

In order to modify the gene encoding the sequence of recombined INSGly(22A)Arg(31B) proinsulin by replacement of GGT (Gly) with TCT (Ser) codon at position 22 of chain A, there were designed following primers for point mutagenesis reaction:

```
        SERG
        5' CAATTCTTAAGGATCCTCTAG 3'
               Ser STOP

SERD
        5' CTTAAGAATTGCAGTAGTTCTCCAG 3'
               Ser
```

Stratagene kit (cat. no 200518-5) has been used to conduct point mutagenesis reaction. Isolation, verification of validity of plasmid nucleotide sequence and obtaining *E. coli* DH5α bacteria with p5/ZUINSSer(22A)Arg(31 B) plasmid have been performed as in Example 1.

Obtained *Escherichia coli* strain is the initial biological material in the process of manufacturing SR insulin via biosynthesis according to Example 12.

EXAMPLE 4

Construction of p5/ZUINSAla(22A) Plasmid and Obtaining of astrain Transformed with it.

To construct a gene of recombined INSAla(22A) proinsulin there has been used 5/ZUINS plasmid. The difference between the gene of recombined INSAla(22A) proinsulin and the model human proinsulin gene is addition of GCT codon to the C terminus of chain A of the former. In result the amino acid sequence of chain A is elongated at position 22 with Ala-alanine amino acid residue.

In order to modify the gene encoding the sequence of recombined human insulin by addition of GCT (Ala) codon at its C terminus, there were designed following primers for point mutagenesis:

```
        ALAG
        5' CAATGCTTAAGGATCCTCTAG 3'
               Ala STOP

ALAD
        5' CTTAAGCATTGCAGTAGTTCTCCAG 3'
               Ala
```

Stratagene kit (cat. no 200518-5) has been used to conduct point mutagenesis reaction. Isolation, verification of validity of plasmid nucleotide sequence and obtaining *E. coli* DH5α bacteria with p5/ZUINSAla(22A) plasmid have been performed as in Example 1.

Obtained *Escherichia coli* strain is the initial biological material in the process of manufacturing AKR insulin via biosynthesis according to Example 13.

EXAMPLE 5

Construction of p5/ZUINSGly(22A)Glu(3B) Plasmid and Obtaining of a Strain Transformed with it To construct a gene of recombined p5/ZUINSGly(22A)Glu(3B) proinsulin there was used p5/ZUINSGly(22A) plasmid. The difference between the gene encoding recombined INSGly(22A)Glu(3B) proinsulin and the gene encoding recombined INSGly(22A) proinsulin is a replacement of AAC (Asn) codon with GAA (Glu) codon at position 3 of chain B.

In order to modify the gene encoding the sequence of recombined INSGly(22A) proinsulin by replacement of AAC (Asn) with GAA (Glu) codon at position 3 of chain B, there were designed following primers for point mutagenesis reaction:

```
        GLUG
        5' GTCGAACAGCACCTGTGTGGTTC 3'
               Glu

GLUD
        5' GCTGTTCGACAAAACGAGGACCTGC 3'
               Glu
```

Stratagene kit (cat. no 200518-5) has been used to conduct point mutagenesis reaction. Isolation, verification of validity of plasmid nucleotide sequence and obtaining *E. coli* DH5α bacteria with p5/ZUINSGly(22A)Glu(31 B) plasmid have been performed as in Example 1.

Obtained *Escherichia coli* strain is the initial biological material in the process of manufacturing GEKR insulin via biosynthesis according to Example 14.

In examples 1-5 as the plasmid hosts there have been used DH5α *E. coli* bacteria, but in described above, model realisation of the invention there can be used also other *E. coli* strains, for example DH5 or HB101.

EXAMPLE 6

Construction of p6/ZUINSSer(22A) Plasmid and Obtaining of a Strain Transformed with it To construct a gene encoding recombined INSSer(22A) proinsulin there was used p6/ZUINS plasmid, in which DNA fragment encoding precursor of recombined insulin is appended to modified gene encoding synthetic ubiquitin. In the ubiquitin-encoding gene arginine codons have been replaced with alanine codons and to the C terminus of ubiquitin gene there has been added an additional arginine codon. The peptide constituting part of ubiquitin is a carrier for insulin precursor, which conditions high efficiency of fusion protein expression in *E. coli*. The region encoding the modified ubiquitin-human insulin fusion protein is placed under control of pms promoter (WO05066344 A2). The plasmid carries tetracycline resistance gene. To construct p6/ZUINS vector there has been used p5/ZUINS plasmid.

The difference between the gene encoding recombined INSSer(22A) proinsulin and the model human proinsulin gene is that the former has appended additional TCT codon at C terminus of chain A. In result amino acid sequence of chain A is elongated at position 22 with Ser-serine amino acid residue.

In order to modify the gene encoding the sequence of recombined proinsulin by appending TCT (Ser) codon at its C terminus, there were designed following primers for point mutagenesis reaction:

```
SKRG
5' GAACTACTGCAATTCTTAAGTCGA 3'
            Ser STOP

SKRD
5' TAGAGTCGACTTAAGAATTGCAGTA 3'
            Ser
```

Stratagene kit (cat. no 200518-5) has been used to conduct point mutagenesis reaction, as the template has been used p6/ZUINS plasmid DNA. *Escherichia coli* DH5α competent cells have been transformed with the reaction mixture. p6/ZUINSSer(22A) plasmid has been isolated and sequenced in order to verify presence of TCT nucleotides encoding serine and correctness of the plasmid sequence. The plasmid with the modified gene encoding p6/ZUINSSer(22A) proinsulin has been used to transform *E. coli* DH5α bacteria. Subsequently the bacteria were cultivated for 18 hours in LB media with addition of tetracycline (0.01 mg/ml) in 500 ml volume at 37° C., 200 rpm. Bacteria material has been preparated for strain bank samples containing 1:1 bacterial cultures and 40% glycerol have been deposited at −70° C.

Obtained *Escherichia coli* strain constitutes initial biological material in the process of manufacturing SKR insulin via biosynthesis according to Example 15.

Genetic construction of p6/ZUINSSer(22A) plasmid p6/ZUINSSer(22A) plasmid is 4911 base pairs long and is made of following regulatory sequences and genes:

from 146 by to 1336 by there is a tetracycline resistance gene TET R, from 4304 by to 4469 by there is a region encoding pms promoter, from 4473 by to 4703 by there is a region encoding the gene encoding the modified synthetic ubiquitin; there are following modifications: replacement of arginine amino acid at positions 42, 54, 72, 74 in the ubiquitin gene with alanine and addition of arginine at position 77 which allows to remove the ubiquitin, from 4704 by to 4868 by there is a sequence encoding the gene encoding recombined INSSer(22A) proinsulin, from 4875 by to 4911 by there is a region encoding transcription terminator Ter.

Structure of p6/ZUINSSer(22A) plasmid containing the gene encoding recombined human insulin protein (SKR protein) is shown schematically in FIG. 3, and its nucleotide and amino acid sequence in FIG. 4.

EXAMPLE 7

Construction of p6/ZUINSGly(22A) Plasmid and Obtaining of astrain Transformed with it.

To construct a gene encoding recombined INSGly(22A) proinsulin there was used p6/ZUINS plasmid, in which DNA fragment encoding precursor of recombined insulin is appended to modified gene encoding synthetic ubiquitin.

The difference between the gene encoding recombined INSGly(22A) proinsulin and the model human proinsulin gene is that the former has appended additional GGT codon at C terminus of chain A. In result amino acid sequence of chain A is elongated at position 22 with Gly—glycine amino acid residue.

In order to modify the gene encoding the sequence of recombined human proinsulin by appending GGT (Gly) codon at its C terminus, there were designed following primers for point mutagenesis reaction:

```
GLYG
5' AACTACTGCAATGGTTAAGTCGACTCTAGC 3'
              Gly STOP

GLYD
5' GTAGCTAGAGTCGACTTAACCATTGCAG 3'
                     Gly
```

Stratagene kit (cat. no 200518-5) has been used to conduct point mutagenesis reaction. Isolation, verification of validity of plasmid nucleotide sequence and obtaining *E. coli* DH5 bacteria with p6/ZUINSGly(22A) plasmid have been performed as in Example 6.

Obtained *Escherichia coli* strain constitutes initial biological material in the process of manufacturing GKR insulin via biosynthesis according to Example 16.

EXAMPLE 8

Construction of p6/ZUINSGly(22A)Glu(3B) Plasmid and Obtaining of a Strain Transformed with it.

To construct a gene of recombined INSGly(22A)Glu(3B) proinsulin there has been used p6/ZUINSGly(22A) plasmid. The difference between the gene of recombined INSGly(22A)Glu(3B) proinsulin and the recombined INSGly(22A) proinsulin gene is replacement of AAC (Asn) codon with GAA (Glu) codon at position 3 of chain B.

In order to modify the gene encoding the sequence of recombined INSGly(22A) proinsulin by replacement of AAC (Asn) codon with GAA (Glu) codon at position 3 in chain B, there were designed following primers for point mutagenesis:

```
GLUG
5' GTCGAACAGCACCTGTGTGGTTC 3'
      Glu

GLUD-2
5' CACAGGTGCTGTTCGACAAAACGACC 3'
              Glu
```

Stratagene kit (cat. no 200518-5) has been used to conduct point mutagenesis reaction. Isolation, verification of validity of plasmid nucleotide sequence and obtaining *E. coli* DH5 bacteria with p6/ZUINSGly(22A)Glu(31 B) plasmid have been performed as in Example 6.

Obtained *Escherichia coli* strain is the initial biological material in the process of manufacturing GEKR insulin via biosynthesis according to Example 17.

EXAMPLE 9

Construction of p6/ZUINSGly(22A)Arg(31B) Plasmid and Obtaining of a Strain Transformed with it To construct a gene of recombined INSGly(22A)Arg(31B) proinsulin there has been used p6/ZUINSGly(22A) plasmid. The gene encoding recombined INSGly(22A)Arg(31B) proinsulin is characterised by this, that it has replaced AAG (Lys) codon with CGT (Arg) codon at position 31 of chain B.

In order to modify the gene encoding the sequence of recombined INSGly(22A) proinsulin there were designed following primers for point mutagenesis:

```
ARGG
5' CTAAAACACGTCGCGGCATCGTTGAACAG 3'
          Arg

ARGD
5' CGATGCCGCGACGTGTTTTAGGAGTGTAG 3'
            Arg
```

Stratagene kit (cat. no 200518-5) has been used to conduct point mutagenesis reaction. Isolation, verification of validity of plasmid nucleotide sequence and obtaining E. coli DH5 bacteria with p6/ZUINSGly(22A)Arg(31B) plasmid have been performed as in Example 6.

Obtained Escherichia coli strain is the initial biological material in the process of manufacturing GR insulin via biosynthesis according to Example 18.

EXAMPLE 10

Manufacturing of GKR Insulin

GKR insulin has been manufactured in a biosynthesis process realised in the classical way (inoculum, seed culture, production culture) using Escherichia coli strain with a DNA fragment encoding GKR insulin precursor obtained according to Example 1. Production cultivation has been conducted in 150 dm$^3$ fermentation tank for 20 hours at 37° C., controlling pH, temperature, optical density, glucose concentration and aeration. In the fermentation conditions GKR analogue has been produced intracellulary in inclusion bodies. After the end of fermentation the fermentation broth has been concentrated and subsequently digested with lysosyme and bacterial cells have been subjected to disintegration. Obtained suspension has been diluted with water and after incubation with Triton centrifuged. Created raw deposit of inclusion bodies was initially purified, finally obtaining inclusion bodies homogenate.

The obtained homogenate has been dissolved (10-15 mg/cm$^3$) in the solution of sodium carbonate with addition of EDTA, subjected to renaturation and, for protection of lysine free amino groups, subjected to reversible process of citraconylation in a reaction with citraconic anhydride. The dissolved protein had been subjected to trypsin digestion in order to cleave the leader protein out and to cleave the insulin chains. In the result of trypsine activity there was obtained GKR insulin. The solution after digestion with trypsine has been subjected to purification with low pressure liquid chromatography on DEAE Sepharose FF gel, and subsequently diafiltration and concentration—second low pressure liquid chromatography on Q Sepharose FF gel. Main fraction has been subjected to purification with high pressure liquid chromatography on Kromasil-RPC8 100A 10μm gel. Main fraction has been concentration using dialysis to concentration of 30-40 mg/cm$^3$ and purified GKR insulin has been separated by crystallisation, using sodium citrate, zinc acetate, citric acid. From one batch of inclusion bodies has been obtained about 5.4 g of crystallised GKR insulin of HPLC purity 97%.

The product's structure has been confirmed by following data:
  molecular mass determined by mass spectroscopy is equal to 6149 and conforms to the theoretical value (6149.1);
  peptide map: conforms;
  sequence and amino acid composition: conforming to theoretical.
Isoelectric point determined by capillary electrophoresis is 7.19.

EXAMPLE 11

Manufacturing of GR Insulin

Proceeding analogously to Example 10, using Escherichia coli strain with DNA fragment encoding GR insulin precursor, obtained in accordance with Example 2, there has been obtained from analogous batch of inclusion bodies 5.2 g of GR insulin of HPLC purity equal to 97.5%.
Product's structure has been confirmed by following data:
  molecular mass determined by mass spectroscopy equals 6021 and conforms to theoretical value (6020.9);
  peptide map: conforms,
  sequence and amino acid composition: conform to theoretical.
Isoelectric point: 6.39.

EXAMPLE 12

Manufacturing of SR Insulin

Proceeding analogously to Example 10, using Escherichia coli strain with DNA fragment encoding SR insulin precursor, obtained in accordance with Example 3, there has been obtained from analogous batch of inclusion bodies 5.5 g of SR insulin of HPLC purity equal to 97%.
Product's structure has been confirmed by following data:
  molecular mass determined by mass spectroscopy equals 6051 and conforms to theoretical value (6050.9);
  peptide map: conforms,
Isoelectric point: 6.55.

EXAMPLE 13

Manufacturing of AKR Insulin

Proceeding analogously to Example 10, using Escherichia coli strain with DNA fragment encoding AKR insulin precursor, obtained in accordance with Example 4, there has been obtained from analogous batch of inclusion bodies 4.7 g of AKR insulin of HPLC purity equal to 96.5%.
Product's structure has been confirmed by following data:
  molecular mass determined by mass spectroscopy equals 6163 and conforms to theoretical value (6163.1);
  peptide map: conforms.
Isoelectric point: 7.07.

EXAMPLE 14

Manufacturing of GEKR Insulin

Proceeding analogously to Example 10, using Escherichia coli strain with DNA fragment encoding GEKR insulin precursor, obtained in accordance with Example 5, there has been obtained from analogous batch of inclusion bodies 5.0 g of GEKR insulin of HPLC purity equal to 97.5%.

Product's structure has been confirmed by following data:
molecular mass determined by mass spectroscopy equals 6164 and conforms to theoretical value (6164.1);
peptide map: conforms.
Isoelectric point: 6.29.

EXAMPLE 15

Manufacturing of SKR Insulin

Proceeding analogously to Example 10, using *Escherichia coli* strain with DNA fragment encoding SKR insulin precursor, obtained in accordance with Example 6, there has been obtained from analogous batch of inclusion bodies 5.3 g of SKR insulin of HPLC purity equal to 98%.
Product's structure has been confirmed by following results:
molecular mass determined by mass spectroscopy equals 6179 and conforms to theoretical value (6179.1);
peptide map: conforms,
Isoelectric point: 7.05.

EXAMPLE 16

Manufacturing of GKR Insulin

Proceeding analogously to Example 10, using *Escherichia coli* strain with DNA fragment encoding GKR insulin precursor, obtained in accordance with Example 7, there has been obtained from analogous batch of inclusion bodies 6.3 g of GKR insulin of HPLC purity equal to 95.5%.
Remaining properties of the product (GKR insulin) as in Example 10.

EXAMPLE 17

Manufacturing of GEKR Insulin

Proceeding analogously to Example 10, using *Escherichia coli* strain with DNA fragment encoding GEKR insulin precursor, obtained in accordance with Example 8, there has been obtained from analogous batch of inclusion bodies 6.0 g of GEKR insulin of HPLC purity equal to 97%.
Remaining properties of the product (GEKR insulin) as in Example 14.

EXAMPLE 18

Manufacturing of GR Insulin

Proceeding analogously to Example 10, using *Escherichia coli* strain with DNA fragment encoding GR insulin precursor, obtained in accordance with Example 9, there has been obtained from analogous batch of inclusion bodies 5.5 g of GR insulin of HPLC purity equal to 96.5%.
Remaining properties of the product (GR insulin) as in Example 11.

EXAMPLE 19

Manufacturing of ZKR Insulin

To 1000 ml of GKR insulin solution manufactured according to Example 10 or 16 (concentration 0.1 mg/ml), in 100 mM MES/KOH buffer pH 5.0-5.5 there has been added 1 μM $CuSO_4$, 100 μg/ml catalase, 5 mM ascorbic acid and 2 μM PAM enzyme (obtained according to Satani M., Takahashi K., Sakamoto H., Harada S., Kaida Y., Noguchi M.; Expression and characterization of human bifunctional peptidylglycine alpha-amidating monooxygenase. *Protein Expr Purif.* 2003 Apr; 28(2):293-302.), and subsequently mixture have been left for 2 hours at 37° C. The reaction has been stopped by addition of 1 mM $Na_2EDTA$.

After filtration the obtained solution has been subjected to purification with ion-exchange chromatography and HPLC methods.

Main fraction containing ZKR insulin concentrated and subjected to crystallisation using sodium citrate, zinc citrate, citric acid. From one batch of reaction mixture there has been obtained about 10 mg of crystalline ZKR insulin of HPLC purity of 97%.
Product's structure has been confirmed by following results:
molecular mass determined by mass spectroscopy equals 6091 and conforms to theoretical value (6091.1);
peptide map: conforms.
Isoelectric point: 7.54.

Example 20

Manufacturing of ZR Insulin

To 100 ml of GR insulin solution, manufactured according to Example 11 or 18 (2 mg/ml), in 100 mM MES/KOH buffer, pH 4.5, there has been added 1 μM $CuSO_4$, 100 μg/ml catalase, 5 mM ascorbic acid and 2 μM PAM enzyme, and subsequently the solution has been mildly mixed for 1 hour at 37° C. The reaction has been stopped by addition of 1 mM $Na_2EDTA$. The solution after reaction with PAM has been subjected to purification by ion-exchange and HPLC methods.

The main fraction containing insulin concentrated and subjected to crystallisation using sodium citrate, zinc citrate, citric acid. From one batch of reaction mixture there was obtained 22 mg of crystalline ZR insulin of HPLC purity of 98%.
Product's structure has been confirmed by following results:
molecular mass determined by mass spectroscopy equals 5963 and conforms to theoretical value (5962.9);
peptide map: conforms.
Isoelectric point: 6.97.

EXAMPLE 21

Manufacturing of pharmaceutical preparation of GKR insulin (100 u/ml)

There was made 100 ml of pharmaceutical preparation of GKR insulin (100 u/ml) of following composition (values per 1.0 ml):

| | |
|---|---|
| GKR insulin (Example 16) | 3.69 mg/ml (as 100% substance, 100 u/ml) |
| m-cresol | 2.7 mg/ml |
| anhydrous glycerine | 16 mg/ml |
| zinc | 30 μg/ml |
| water for injection | to 10 ml |
| pH | 4.5 |

Preparation Procedure was as Follows:

There were made two following solutions:
Solution 1
Zinc oxide in amount necessary to reach the final concentration of Zn ions of 30 µg/ml were dissolved in 40 ml of 10 mM hydrochloric acid. After that, to obtained solution was added insulin GKR in amount corresponding to 10 000 u of insulin GKR, under mild stirring until obtaining a clear solution and then pH adjusted to value 4,5.
Solution 2
Separately, 270 mg of m-cresol and 1600 ml of anhydrous glycerol were dissolved in 40 ml water for injection.
Mixing of solutions 1 and 2
Solution 1 was added under stirring to Solution 2, supplemented with water for injection to volume 100 ml and in case of need corrected pH to value 4,5 with 10 mM hydrochloric acid or 0.2 M solution of sodium hydroxide. Resulting mixture was in sterile condition filtered through 0.22 pm filter and aliquoted into glass 3 ml vials. It was determined that the preparation containing GKR insulin (100 u/ml) exhibits stability in room temperature investigated period of 56 days, in the accelerated stability test (Example 24).

EXAMPLE 22

Manufacturing of Pharmaceutical Preparation of GR Insulin (100 u/ml)

There was made 100 ml of pharmaceutical preparation of GR insulin (100 u/ml) of the following composition (values per 1.0 ml):

| | |
|---|---|
| GR insulin (Example 11) | 3.61 mg/ml (as 100% substance, 100 u/ml) |
| m-cresol | 2.7 mg/ml |
| anhydrous glycerine | 16 mg/ml |
| zinc | 30 µg/ml |
| injection water | up to 1.0 ml |
| pH | 4.0 |

The procedure was identical as in Example 21, apart of that that instead of GKR insulin there was used GR insulin (in the amount of 361 mg, 10 000 u) and that the final value of pH was 4.0.

EXAMPLE 23

Manufacturing of Pharmaceutical Preparation of GEKR Insulin (100 u/ml)

There was made 100 ml of pharmaceutical preparation of GEKR insulin (100 u/ml) of the following composition (values per 1.0 ml):

| | |
|---|---|
| GEKR insulin (Example 14) | 3.70 mg/ml (as 100% substance, 100 u/ml) |
| m-cresol | 2.7 mg/ml |
| anhydrous glycerine | 16 mg/ml |
| zinc | 30 µg/ml |
| injection water | up to 1.0 ml |
| pH | 4.0 |

The procedure was identical as in Example 21, apart of that that instead of GKR insulin there was used GEKR insulin (in the amount of, 10 000 u) and that the final value of pH was 4.0.

EXAMPLE 24

Examination of Accelerated Stability of Pharmaceutical Preparation of GKR insulin (100 u/ml)

Pharmaceutical preparation of GKR insulin (100 u/ml), made according to Example 21, has been subjected to examination of accelerated stability (25° C.±2° C.). During this examination there were performed analysis of purity and level of protein contamination. Below there are exhibited HPLC purity of the product (GKR insulin) and the proportional contribution: highest single contamination, deamido derivative and polymers, in HPLC test, in time points of: "0", 28, 42 and 56 days.

| HPLC purity test | "0" | 28 days | 42 days | 56 days |
|---|---|---|---|---|
| Main peak [%] | 95.10 | 94.33 | 93.98 | 93.60 |
| Highest single contamination [%] | 1.07 | 1.70 | 1.72 | 1.98 |
| Deamido [%] | 0.28 | 0.37 | 0.32 | 0.36 |
| Polymers [%] | 0.17 | 0.37 | 0.44 | 0.48 |

EXAMPLE 25

Examination of Accelerated Stability of Pharmaceutical Preparation of GEKR Insulin (100 u/ml)

Pharmaceutical preparation of GEKR insulin (100 u/ml), made according to Example 23, has been subjected to examination of accelerated stability (25° C.±2° C.). During this examination there were performed analysis of purity and level of protein contamination. Below there are exhibited HPLC purity of the product (GEKR insulin) and the proportional contribution: highest single contamination, and polymers, in HPLC test, in time points of: "0", and 14 days and 1, 2 and 3 months.

| HPLC purity test | "0" | 14 days | 1 months | 2 months | 3 months |
|---|---|---|---|---|---|
| Main peak[%] | 97.33 | 97.14 | 96.42 | 94.55 | 94.41 |
| Highest single contamination [%] | 0.55 | 0.45 | 0.67 | 1.08 | 1.26 |
| Polymers[%] | not determined | 0.09 | not determined | 0.50 | not determined |

EXAMPLE 26

Determination of GKR Activity on Normoglycaemic Animals

Recombined human insulin analogue (GKR insulin), similarly to Gensulin N (recombined isophane human insulin) exhibits prolonged activity time, and hypoglycaemic of normoglycaemic rats has similar course. Significant differences in hypoglycaemic activity of both preparations have been observed in 0.5 and 1 hour after administration. In this time there is observed fast and deep decrease of glucose concentration after GKR insulin. Peak activity of GKR insulin and Gensulin N is in $2^{nd}$ hour.

Initial research confirmed that GKR insulin is an active analogue of prolonged hypoglycaemic activity. Decrease in glucose level after GKR insulin administration was observed for up to 12 hours, while levels of glucose after 24 hours were similar to initial. Results of reaction of normoglycaemic rats to single administration of GKR insulin and Gensulin N preparations (taking into account mean values±SEM) are shown in Table 1 and FIG. 5.

EXAMPLE 27

Determination of GKR Insulin Activity on Animals with Experimental Diabetes

Studies on experimental model of rat diabetes (induction with streptozotocin) confirmed irrefutably hypoglycaemic activity of GKR insulin. This activity has properties of prolonged activity.

After single dose administration, the lowering of glucose concentration in blood of the examined rats remains statistically significant up to $8^{th}$-$10^{th}$ hour (depending on intensity of diabetes and dose), in comparison with control. During the research there was demonstrated faster beginning of activity and faster achieving of peak activity (beginning 30 mins, peak 1-2 hours) by GKR insulin compared to the reference preparation—insulin glargine (Lantus). Statistical significance of this phenomenon has been confirmed in severe and moderate diabetes.

Also the research of multiple dose administration of GKR insulin and the reference preparation of insulin glargine demonstrated similar activity of that both analogues. Administered for 21 days, three times per day, preparations caused improvement of glycaemy parameters in mild diabetes and, in principle, did not differ statistically in the intensity of the effect. The only difference was noticeably more equalised activity profile of GKR insulin.

Additionally there was observed very interesting phenomenon of long-lasting hypoglycaemic effect after termination of administration of GKR preparation. This observation has been conducted on 9 rats treated with GKR preparation and 3 treated with Lantus, of the group with mild diabetes, who were administered analogues in the dose of 5 u/kg bm for 21 days. Obtained results can be an evidence of existence of very strong bounding of GKR insulin in tissues (possibly subcutaneous tissue). They support thesis of existence of compartment, in which insulin is accumulated and slowly redistributed. This phenomenon was not observed for the reference preparation. This property, after its confirmation in humans, could be a breakthrough in therapy with prolonged activity insulin analogues, allowing e.g. administration of less than one dose of the medicine per day.

The results describing glucose concentration in rat blood after single dose administration of GKR insulin in the dose of 5 u/kg bm in the mild streptozotocin-induced diabetes model (in comparison with Lantus preparation) are shown in Table 2 and FIG. 6.

The results describing influence of GKR insulin on glucose concentration in rat blood after single dose one-time administration of doses 2.5 u/kg bm, 5 u/kg bm and 7.5 u/kg bm in severe streptozotocin-induced diabetes model (in comparison with Lantus preparation and control) are shown in Table 3.

The results presenting influence of GKR insulin on glucose concentration in rat blood after single dose administration of doses 2.5 u/kg bm, 5 u/kg bm and 7.5 u/kg bm in severe streptozotocin-induced diabetes model (in comparison with control) are shown in FIG. 7.

The results presenting influence of GKR insulin on glucose concentration in rat blood after single dose administration of 7.5 u/kg bm in severe streptozotocin-induced diabetes model (in comparison with Lantus preparation) are shown in FIG. 8.

The results describing glucose concentration in rat blood after multiple dose administrations of 5 u/kg bm of GKR insulin in mild streptozotocin-induced diabetes model (in comparison with Lantus preparation) are shown in Table 4 and FIG. 9.

The results describing glucose concentration in rat blood after termination of administrations of 5 u/kg bm of GKR insulin in mild streptozotocin-induced diabetes model (in comparison with Lantus preparation) are shown in Table 5 and FIG. 10.

TABLE 1

Influence of single dose administration of GKR insulin (in the dose of 5 u/kg bm) on glucose concentration in blood of normoglycaemic rats, in comparison with Gensulin N (isophane recombined human insulin).

| Tested preparation | Dose [u/kg bm] | Glucose concentration in blood [mg/dl]* | | | | | | | | | Number of animals in groups |
|---|---|---|---|---|---|---|---|---|---|---|---|
| | | Before administration | time of determination in hours after administration | | | | | | | | |
| | | | 0.5 | 1 | 2 | 4 | 6 | 8 | 10 | 12 | |
| GKR insulin | 5 | 87.5 ± 1.0 | 45.3 ± 3.64** ^^ | 32.8 ± 1.3** ^^ | 26.7 ± 3.5** | 41.2 ± 4.1** | 58.2 ± 2.0** | 60.7 ± 2.9** | 59.6 ± 1.9** | 65.8 ± 2.7** | 10*** |
| Gensulin N | 2 | 87.6 ± 3.7 | 81.2 ± 4.2 | 55.6 ± 4.3## | 39.1 ± 4.4## | 33.8 ± 5.1## | 46.8 ± 5.4## | 51.3 ± 5.0## | 65.3 ± 3.2## | 70.7 ± 3.5## | 10 |
| 0.9% NaCl solution control | Volume s.c., 3 ml/ 300 g bm | 91.5 ± 2.0 | 87.0 ± 2.1 | 88.7 ± 1.7 | 88.9 ± 2.0 | 87.4 ± 3.2 | 88.7 ± 2.2 | 93.0 ± 2.0 | 91.3 ± 2.2 | 93.0 ± 2.9 | 10 |

Experimental groups n = 10; *mean values ± SEM;
Statistical significance **p < 0.01 GKR insulin vs. initial glucose concentration; ##p < 0.01, #p < 0.05 Gensulin N vs. initial glucose concentration; ^^p < 0.01 GKR insulin 5 u/kg bm vs. Gensulin N 2 u/kg bm.
***Noted death of one animal in the $2^{nd}$ hour.

TABLE 2

Influence of single dose administration of GKR insulin in a dose of 5 u/kg bm on glucose concentration in blood of rats with mild streptozotocyn-induced diabetes, compared with Lantus preparation (insulin glargine).

| diabetes model | Tested preparation | dose s.c. | number of rats in the group | normo-glycae-my | fixed hyper-glycae-my | \multicolumn{10}{c}{concentration of glucose in rat blood mean value (mg/dl) ± SEM} |
| --- | --- | --- | --- | --- | --- | --- | --- | --- | --- | --- | --- | --- | --- | --- |
| | | | | | | \multicolumn{10}{c}{time of blood sampling after single dose administration of the preparation (hours)} |
| | | | | 0 | | 0.5 | 1 | 2 | 4 | 6 | 8 | 10 | 12 | 24 | 36 |
| mild strepto-zotocyn-induced - 32 mg/kg bm., i.m.) | GKR | 5 u/kg bm | 20 | 82.5 ± 3.0 | 250.7 ± 22.2 | 115.6 ± 16.1^^ | 84.1 ± 7.8^^ | 93.3 ± 4.8^^ | 106.7 ± 7.2^^ | 117.0 ± 4.9**^^ | 130.3 ± 6.9^^ | 142.0 ± 7.9^^ | 173.4 ± 18.6 | 209.2 ± 20.4 | 218.2 ± 16.8 |
| | Lantus | | 9 | 103.6 ± 2.9 | 229.2 ± 32.5 | 135.6 ± 27.1 | 72.6 ± 5.2 | 69.7 ± 8.4 | 77.9 ± 6.8 | 76.8 ± 5.7 | 106.1 ± 6.0 | 128.2 ± 13.1 | 199.8 ± 36.6 | 224.3 ± 28.8 | 228.7 ± 29.7 |
| | control | 10 nl/200 g bm | 9 | 91.3 ± 5.9 | 236.1 ± 7.7 | 222.2 ± 24.8 | 205.3 ± 21.5 | 207.4 ± 21.8 | 203.4 ± 20.4 | 205.9 ± 21.3 | 212.0 ± 24.1 | 213.6 ± 23.1 | 213.2 ± 25.6 | 214.8 ± 23.0 | 215.7 ± 24.7 |

Statistical significance:

**p < 0.01

*p < 0.05 GKR vs. Lantus

^^p < 0.01

^p < 0.05 GKR vs. control

TABLE 4

Influence of multiple administrations of GKR insulin at a dose of 5 u/kg bm on glucose concentration in blood of rats with mild streptozotocin-induced diabetes compared with Lantus preparation (insulin glargine).

| Tested preparation | number of rats in the group | normo-gly-caemia | fixed hyper-glycaemia | \multicolumn{10}{c}{glucose concentration in blood of the rats, mean value (mg/dl) ± SEM} |
| --- | --- | --- | --- | --- | --- | --- | --- | --- | --- | --- | --- | --- | --- |
| | | | | \multicolumn{10}{c}{consecutive days of study} |
| | | | | 1 | 2 | 3 | 4 | 5 | 6 | 7 | 8 | 9 | 10 |
| GKR 5 u/kg bm | 20 | 82.5 ± 3.0 | 198.1 ± 12.1 | 155.4 ± 7.1^ | 156.8 ± 6.2^ | 157.7 ± 7.4^ | 148.1 ± 4.5**^^ | 144.1 ± 5.3^ | 151.6 ± 5.5^ | 156.6 ± 6.0^ | 152.9 ± 5.7^ | 147.0 ± 3.2^ | 152.3 ± 3.8^ |
| Lantus 5 u/kg bm. | 9 | 103.6 ± 2.9 | 228.9 ± 30.7 | 136.3 ± 8.1 | 147.0 ± 9.0 | 173.7 ± 10.4 | 184.9 ± 12.7 | 163.7 ± 11.2 | 175.8 ± 10.4 | 171.4 ± 8.8 | 168.4 ± 15.7 | 142.9 ± 20.3 | 160.4 ± 14.4 |
| control 10 nl/200 g bm | 5 | 88.8 ± 9.4 | 243.4 ± 4.7 | 229.4 ± 13.3 | 232.6 ± 10.6 | 227.0 ± 9.9 | 254.4 ± 9.1 | 257.0 ± 8.2 | 247.0 ± 32.7 | 258.0 ± 6.7 | 257.0 ± 7.9 | 259.8 ± 12.4 | 252.0 ± 6.7 |

| Tested preparation | number of rats in the group | normo-gly-caemia | fixed hyper-glycaemia | \multicolumn{11}{c}{glucose concentration in blood of the rats, mean value (mg/dl) ± SEM} |
| --- | --- | --- | --- | --- | --- | --- | --- | --- | --- | --- | --- | --- | --- | --- |
| | | | | \multicolumn{11}{c}{consecutive days of study} |
| | | | | 11 | 12 | 13 | 14 | 15 | 16 | 17 | 18 | 19 | 20 | 21 |
| GKR 5 u/kg bm. | 20 | 82.5 ± 3.0 | 198.1 ± 12.1 | 152.6 ± 2.3^ | 153.6 ± 2.9^ | 149.7 ± 3.1^ | 151.5 ± 3.3^ | 151.1 ± 3.4^ | 149.0 ± 5.6^ | 142.7 ± 3.2**^^ | 143.0 ± 4.9^ | 149.7 ± 4.7^ | 149.9 ± 4.3^ | 149.2 ± 4.2*^^ |
| Lantus 5 u/kg bm. | 9 | 103.6 ± 2.9 | 228.9 ± 30.7 | 164.8 ± 13.9 | 170.6 ± 19.3 | 161.6 ± 15.6 | 144.0 ± 18.3 | 124.9 ± 14.7 | 156.7 ± 7.5 | 191.3 ± 19.1 | 141.0 ± 11.4 | 172.1 ± 33.1 | 145.7 ± 15.1 | 132.2 ± 8.9 |
| control 10 nl/200 g bm | 5 | 88.8 ± 9.4 | 243.4 ± 4.7 | 248.4 ± 8.4 | 255.0 ± 5.5 | 260.0 ± 11.7 | 252.0 ± 14.9 | 249.6 ± 20.4 | 256.2 ± 8.8 | 255.0 ± 19.4 | 259.4 ± 16.7 | 233.6 ± 11.4 | 270.2 ± 11.0 | 268.8 ± 3.7 |

Statistical significance:

**p < 0.01

*p < 0.05 GKR vs. Lantus

^^p < 0.01

^p < 0.05 GKR vs. control

TABLE 5

Glucose concentration in the period after termination of administration of
GKR insulin in the dose of 5 u/kg bm in the model of mild streptozotocin-induced,
in comparison with Lantus preparation (insulin glargine).

| | | | | glucose concentration in rat blood, mean value (mg/dl) | | | | | |
|---|---|---|---|---|---|---|---|---|---|
| Tested preparation | normo-glycaemia | fixed hyper-glycaemia | in the last day of administration | days after termination of administration of tested preparations | | | | | |
| | | | | 1 | 2 | 3 | 5 | 8 | 11 |
| GKR 5 u/kg bm | 86.1 ± 3.7 | 214.4 ± 24.3 | 148.3 ± 8.5 | 146.4 ± 9.4 | 136.0 ± 7.8 | 137.4 ± 6.6 | 132.8 ± 3.1 | 123.2 ± 3.1 | 126.4 ± 3.5 |
| Lantus 5 u/kg bm | 103.3 ± 1.2 | 254.0 ± 67.8 | 141.0 ± 18.2 | 282.3 ± 58.2 | 277.7 ± 72.6 | 235.0 ± 89.7 | 158.7 ± 40.3 | 195.3 ± 63.1 | 222.3 ± 86.4 |

TABLE 3

Influence of single dose administration of GKR insulin (in dose of 2.5 u, 5 u and 7.5 u/kg bm) on glucose concentration
in blood of rats with severe streptozotocin-induced diabetes, compared with Lantus preparation (insulin glargine).

| diabetes model | Tested preparation | dose s.c. | number of rats in the group | normo-glycaemy | fixed hyper-glycaemia | glucose concentration in rat blood mean value (mg/dl) ± SEM | | | | | | | | | |
|---|---|---|---|---|---|---|---|---|---|---|---|---|---|---|---|
| | | | | | | time of blood sampling after single dose administration of the preparation (hours) | | | | | | | | | |
| | | | | | 0 | 0.5 | 1 | 2 | 4 | 6 | 8 | 10 | 12 | 24 | 36 |
| severe strepto-zotocin-induced - 45 mg/ kg bm, i.m.) | GKR | 2.5 u/kg bm | 10 | 86.3 ± 3.4 | 570.8 ± 20.1 | 251.4 ± 41.2**^ | 170.2 ± 28.8**^ | 250.0 ± 37.8**^ | 377.4 ± 35.0**^ | 426.0 ± 36.9 | 463.1 ± 42.1 | 524.2 ± 45.3 | 560.1 ± 33.0 | 551.0 ± 40.2 | 576.4 ± 22.7 |
| | Lantus | bm | 10 | 84.4 ± 3.8 | 596.8 ± 3.1 | 376.5 ± 24.3 | 284.3 ± 28.7 | 134.55 ± 22.9 | 209.1 ± 34.4 | 314.6 ± 52.4 | 415.2 ± 40.0 | 502.6 ± 25.5 | 546.4 ± 17.5 | 537.6 ± 23.2 | 584.0 ± 25.8 |
| | GKR | 5 u/kg | 11 | 84.7 ± 4.0 | 585.9 ± 7.5 | 235.3 ± 32.0^ | 122.6 ± 21.1^ | 119.6 ± 11.6^ | 245.2 ± 26.7**^ | 367.4 ± 29.9**^ | 421.1 ± 33.8**^ | 483.5 ± 30.6 | 546.7 ± 40.1 | 594.4 ± 3.8 | 596.0 ± 3.3 |
| | Lantus | bm | 11 | 81.6 ± 3.2 | 572.9 ± 12.6 | 302.3 ± 42.7 | 173.4 ± 33.7 | 123.1 ± 21.4 | 131.3 ± 10.9 | 152.5 ± 14.6 | 262.2 ± 36.7 | 426.7 ± 39.8 | 502.6 ± 26.5 | 580.2 ± 10.5 | 594.6 ± 3.1 |
| | GKR | 7.5 u/kg | 10 | 89.0 ± 3.4 | 573.9 ± 18.8 | 259.1 ± 14.2*^ | 133.1 ± 19.3^ | 109.2 ± 11.8^ | 216.1 ± 32.6**^ | 280.6 ± 42.3^ | 350.6 ± 49.2^ | 508.7 ± 34.0 | 526.4 ± 27.3 | 571.0 ± 20.4 | 583.0 ± 17.0 |
| | Lantus | bm | 10 | 82.4 ± 3.5 | 594.0 ± 6.0 | 335.4 ± 28.5 | 198.3 ± 36.7 | 106.1 ± 22.4 | 105.5 ± 16.8 | 188.7 ± 28.7 | 309.5 ± 54.1 | 402.6 ± 49.3 | 461.6 ± 38.4 | 596.8 ± 3.09 | 599.3 ± 0.7 |
| | control | 10 µl/ 200 g bm | 9 | 74 ± 3.6 | 592.1 ± 5.4 | 578.6 ± 10.2 | 594.2 ± 5.4 | 579.2 ± 13.0 | 548.8 ± 23.5 | 526.0 ± 25.5 | 547.3 ± 23.7 | 544.9 ± 14.0 | 575.3 ± 12.4 | 593.3 ± 6.7 | 594.3 ± 2.6 |

Statistical significance:
**p < 0.01
*p < 0.05 GKR vs. Lantus
^^p < 0.01
^p < 0.05 GKR vs. control

EXAMPLE 28

Determination of GR Insulin Activity in Animals with Experimental Diabetes

Hypoglycaemic activity of GR insulin has been confirmed in a moderate streptozotocin-induced diabetes in rats.

Activity of GR insulin after administration of single doses—5 u or 10 u/kg bm has been determined to be fast and strong. Beginning of activity occurs already after 30 minutes after administration of the preparation and remains at the same level up to 2 hours, and subsequently weakens until reaching initial levels in $24^{th}$-$36^{th}$ hour.

Results describing influence of GR insulin preparation on glucose concentration in blood of rats after single dose administration of 5 u and 10 u/kg bm doses in a model of moderate streptozotocin-induced diabetes (in comparison with Lantus preparation) are shown in Table 6. A plot of glucose concentration/time changes after administration of 5 u/kg bm of GR insulin is shown in FIG. 11.

EXAMPLE 29

Determination of GEKR Insulin Activity in Animals with Experimental Diabetes

Hypoglycaemic activity of GEKR insulin analogue has been confirmed in a preliminary study on a rat streptozotocin-induced diabetes of moderate course.

After single administration of GEKR insulin in a dose of 10 u/kg bm there was observed very quick (already after 0.5 hour), strong activity reducing glucose concentration in animals' blood. This activity peaked already one hour after administration of the preparation and slowly decreases, still causing significant decrease of glucose level in comparison to initial values up to 12 hours after administration. This research was conducted in comparison with Levemir preparation, insulin analogue of prolonged activity (insulin detemir).

Results describing influence of GEKR insulin on glucose concentration in rat blood after single dose administration of 10 u/kg bm in a moderate streptozotocin-induced model of diabetes, in comparison with preparation Levemir, are shown in Table 7, and a plot of glucose concentration change as a function of time after administration 10 u/kg bm of GEKR insulin in FIG. 12.

TABLE 6

Influence of single dose administration of GR insulin (doses of 5 u/kg bm and 10 u/kg bm) on glucose concentration in blood of rats with moderate streptozotocin-induced diabetes in comparison with Lantus preparation (insulin glargine).

| diabetes model | Tested preparation | dose s.c. | number of rats in the group | normoglycaemia | fixed hyperglycaemia | glucose concentration in rat blood mean (mg/dl) ± SEM time of blood sample acquisition after single dose preparation administration (hours) | | | | | | | | | |
|---|---|---|---|---|---|---|---|---|---|---|---|---|---|---|---|
| | | | | | | 0.5 | 1 | 2 | 4 | 6 | 8 | 10 | 12 | 24 | 36 |
| moderate streptozotocin-induced - 40 mg/kg bm i.m.) | GR | 5.0 u/kg bm | 15 | 80.6 ± 2.4 | 507.4 ± 22.9 | 113.9 ± 10.8** | 98.5 ± 7.6 | 92.5 ± 6.7 | 160.3 ± 18.3 | 198.1 ± 22.6* | 268.7 ± 29.3 | 294.9 ± 29.4 | 353.0 ± 28.5 | 406.9 ± 28.3** | 498.4 ± 26.8 |
| | Lantus | bm | 5 | 83.0 ± 4.3 | 600.0 ± 0.0 | 324.8 ± 35.3 | 136.6 ± 27.0 | 102.2 ± 20.4 | 97.2 ± 11.2 | 94.8 ± 5.3 | 157.6 ± 26.7 | 266.6 ± 60.5 | 401.4 ± 60.4 | 600.0 ± 0.0 | 594.0 ± 5.5 |
| | GR | 10 u/kg | 15 | 84.9 ± 3.7 | 498.7 ± 25.4 | 96.1 ± 8.1** | 85.7 ± 4.4** | 77.0 ± 3.5 | 151.5 ± 14.9 | 168.3 ± 21.0 | 200.3 ± 26.2* | 248.9 ± 30.6 | 326.1 ± 27.9 | 389.3 ± 27.6 | 431.6 ± 24.4 |
| | Lantus | bm | 6 | 77.8 ± 2.3 | 550.2 ± 33.9 | 247.8 ± 25.6 | 134.0 ± 21.8 | 75.0 ± 8.1 | 109.3 ± 16.0 | 94.7 ± 20.0 | 103.7 ± 20.9 | 148.8 ± 20.4 | 223.3 ± 42.2 | 389.2 ± 17.8 | 453.7 ± 28.3 |
| | control | 10 ul/200 g bm | 6 | 80.5 ± 2.9 | 509.5 ± 40.6 | 527.2 ± 32.5 | 532.0 ± 30.9 | 495.5 ± 26.8 | 463.5 ± 26.9 | 497.2 ± 23.6 | 452.8 ± 31.8 | 491.7 ± 27.8 | 520.3 ± 31.2 | 503.7 ± 35.5 | 507.7 ± 35.3 |

Statistical significance:
**p < 0.01
*p < 0.05 GR vs. Lantus

TABLE 7

Influence of single dose administration of GEKR insulin (in a dose of 10 u/kg bm) on glucose concentration in blood of rats with moderate diabetes, in comparison with Levemir preparation (insulin detemir).

| diabetes model | Tested preparation and dose s.c. | normoglycaemia | fixed hyperglycaemia | Concentration of glucose in rat blood mean value (mg/dl) ± SEM Time of blood sampling after single dose administration (hours) | | | | | |
|---|---|---|---|---|---|---|---|---|---|
| | | | | 0.5 | 1 | 4 | 6 | 8 | 12 |
| moderate streptozotocin-induced - 40 mg/kg bm, i.m. | GEKR 10 u/kg bm | 90.5 ± 6.4 | 469.5 ± 65.8 | 218.0 ± 19.7 | 109.3 ± 10.1 | 143.7 ± 22.4 | — | 242.3 ± 59.2 | 329.3 ± 155.3 |
| | Levemir 10 u/kg bm | 98.5 ± 3.5 | 502.5 ± 26.2 | — | — | — | 142.3 ± 22.3 | — | 384.0 ± 38.7 |

The invention claimed is:

1. Insulin derivative or its pharmaceutically acceptable salt containing two polypeptides forming chain A and chain B, characterised by being a new polipeptide of the formula 1:

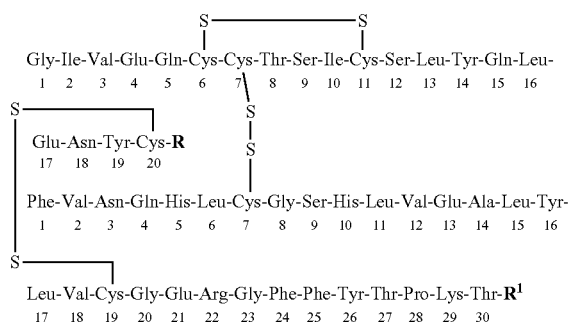

wherein R denotes group of formula Asn-$R^2$, where $R^2$ denotes neutral L-amino acid; and $R^1$ denotes B31Lys-B32Arg, wherein B3Asn can be optionally replaced by B3Glu, or B31Arg, wherein amino acid sequence of chain A has been chosen from SEQ ID NO: 1-3, while amino acid sequence of chain B has been chosen from SEQ ID NO: 7, 9, and 10 in one of the following combinations:

SEQ ID NO: 1 with SEQ ID NO: 7, SEQ ID NO: 1 with SEQ ID NO: 9, SEQ ID NO: 1 with SEQ ID NO: 10, SEQ ID NO: 2 with SEQ ID NO: 7, SEQ ID NO: 3 with SEQ ID NO: 7, SEQ ID NO: 3 with SEQ ID NO: 10, and wherein the new polypeptide of formula 1 is an analogue of recombined human insulin of isoelectric point 5-8.5.

2. Insulin derivative or its pharmaceutically acceptable salt according to claim 1, characterised by $R^2$ denotes a single neutral L-amino acid.

3. Insulin derivative or its physiologically acceptable salt according to claim 2, characterised in that:
R in formula 1 denotes group of formula Asn-$R^2$, where $R^2$ denotes Gly and $R^1$ denotes B31Lys-B32Arg, or
R in formula 1 denotes group of formula Asn-$R^2$, where $R^2$ denotes Ala and $R^1$ denotes B31Lys-B32Arg, or
R in formula 1 denotes group of formula Asn-$R^2$, where $R^2$ denotes Ser and $R^1$ denotes B31Lys-B32Arg, or
R in formula 1 denotes group of formula Asn-$R^2$, where $R^2$ denotes Gly, and $R^1$ denotes B31Arg, or
R in formula 1 denotes group of formula Asn-$R^2$, where $R^2$ denotes Ser, and $R^1$ denotes B31Arg, or.

4. Pharmaceutical composition, characterised in, that it contains effectively acting amount of insulin derivative or its pharmaceutically acceptable salt according to one of claims from 1 to 3.

5. Pharmaceutical composition according to claim 4, characterised in, that it contains 10 up to 50 μg/ml of zinc.

6. Insulin derivative or its pharmaceutically acceptable salt according to claim 1, wherein B3Asn is replaced by Glu.

* * * * *

SEQUENCE LISTING

```
<160> NUMBER OF SEQ ID NOS: 25

<210> SEQ ID NO 1
<211> LENGTH: 22
<212> TYPE: PRT
<213> ORGANISM: artificial
<220> FEATURE:
<223> OTHER INFORMATION: insulin chain A mutant

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn Gly
            20
```

```
<210> SEQ ID NO 2
<211> LENGTH: 22
<212> TYPE: PRT
<213> ORGANISM: artificial
<220> FEATURE:
<223> OTHER INFORMATION: insulin chain A mutant

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn Ala
            20

<210> SEQ ID NO 3
<211> LENGTH: 22
<212> TYPE: PRT
<213> ORGANISM: artificial
<220> FEATURE:
<223> OTHER INFORMATION: insulin chain A mutant

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn Ser
            20

<210> SEQ ID NO 4
<211> LENGTH: 21
<212> TYPE: PRT
<213> ORGANISM: artificial
<220> FEATURE:
<223> OTHER INFORMATION: insulin chain A mutant
<220> FEATURE:
<221> NAME/KEY: MISC_FEATURE
<222> LOCATION: (21)..(21)
<223> OTHER INFORMATION: Xaa = amid Asn

<400> SEQUENCE: 4

Gly Ile Val Glu Gln Cys Cys Thr Ser Ile Cys Ser Leu Tyr Gln Leu
1               5                   10                  15

Glu Asn Tyr Cys Xaa
            20

<210> SEQ ID NO 5
<211> LENGTH: 20
<212> TYPE: PRT
<213> ORGANISM: artificial
<220> FEATURE:
<223> OTHER INFORMATION: insulin chain A mutant
<220> FEATURE:
<221> NAME/KEY: MISC_FEATURE
<222> LOCATION: (20)..(20)
<223> OTHER INFORMATION: Xaa = amid Cys

<400> SEQUENCE: 5

Gly Ile Val Glu Gln Cys Cys Thr Ser Ile Cys Ser Leu Tyr Gln Leu
1               5                   10                  15

Glu Asn Tyr Xaa
            20

<210> SEQ ID NO 6
<211> LENGTH: 22
<212> TYPE: PRT
<213> ORGANISM: artificial sequence
<220> FEATURE:
<223> OTHER INFORMATION: insulin chain A mutant

<400> SEQUENCE: 6
```

```
Gly Ile Val Glu Gln Cys Cys Thr Ser Ile Cys Ser Leu Tyr Gln Leu
1               5                   10                  15

Glu Asn Tyr Cys Asn Thr
            20
```

<210> SEQ ID NO 7
<211> LENGTH: 32
<212> TYPE: PRT
<213> ORGANISM: artificial
<220> FEATURE:
<223> OTHER INFORMATION: insulin chain B mutant

<400> SEQUENCE: 7

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30
```

<210> SEQ ID NO 8
<211> LENGTH: 32
<212> TYPE: PRT
<213> ORGANISM: artificial
<220> FEATURE:
<223> OTHER INFORMATION: insulin chain B mutant

<400> SEQUENCE: 8

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 9
<211> LENGTH: 32
<212> TYPE: PRT
<213> ORGANISM: artificial
<220> FEATURE:
<223> OTHER INFORMATION: insulin chain B mutant

<400> SEQUENCE: 9

```
Phe Val Glu Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30
```

<210> SEQ ID NO 10
<211> LENGTH: 31
<212> TYPE: PRT
<213> ORGANISM: artificial
<220> FEATURE:
<223> OTHER INFORMATION: insulin chain B mutant

<400> SEQUENCE: 10

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg
            20                  25                  30
```

<210> SEQ ID NO 11
<211> LENGTH: 30
<212> TYPE: DNA
<213> ORGANISM: artificial
<220> FEATURE:
<223> OTHER INFORMATION: primer GLYG

<400> SEQUENCE: 11

```
aactactgca atggttaagt cgactctagc                                      30

<210> SEQ ID NO 12
<211> LENGTH: 28
<212> TYPE: DNA
<213> ORGANISM: artificial
<220> FEATURE:
<223> OTHER INFORMATION: primer GLYD

<400> SEQUENCE: 12
gtagctagag tcgacttaac cattgcag                                        28

<210> SEQ ID NO 13
<211> LENGTH: 29
<212> TYPE: DNA
<213> ORGANISM: artificial
<220> FEATURE:
<223> OTHER INFORMATION: primer ARGG

<400> SEQUENCE: 13
ctaaaacacg tcgcggcatc gttgaacag                                       29

<210> SEQ ID NO 14
<211> LENGTH: 29
<212> TYPE: DNA
<213> ORGANISM: artificial
<220> FEATURE:
<223> OTHER INFORMATION: primer ARGD

<400> SEQUENCE: 14
cgatgccgcg acgtgtttta ggagtgtag                                       29

<210> SEQ ID NO 15
<211> LENGTH: 21
<212> TYPE: DNA
<213> ORGANISM: artificial
<220> FEATURE:
<223> OTHER INFORMATION: primer SERG

<400> SEQUENCE: 15
caattcttaa ggatcctcta g                                               21

<210> SEQ ID NO 16
<211> LENGTH: 25
<212> TYPE: DNA
<213> ORGANISM: artificial
<220> FEATURE:
<223> OTHER INFORMATION: primer SERD

<400> SEQUENCE: 16
cttaagaatt gcagtagttc tccag                                           25

<210> SEQ ID NO 17
<211> LENGTH: 21
<212> TYPE: DNA
<213> ORGANISM: artificial
<220> FEATURE:
<223> OTHER INFORMATION: primer ALAG

<400> SEQUENCE: 17
caatgcttaa ggatcctcta g                                               21

<210> SEQ ID NO 18
<211> LENGTH: 25
<212> TYPE: DNA
<213> ORGANISM: artificial
```

```
<220> FEATURE:
<223> OTHER INFORMATION: primer ALAD

<400> SEQUENCE: 18
cttaagcatt gcagtagttc tccag                                          25

<210> SEQ ID NO 19
<211> LENGTH: 23
<212> TYPE: DNA
<213> ORGANISM: artificial
<220> FEATURE:
<223> OTHER INFORMATION: primer GLUG

<400> SEQUENCE: 19
gtcgaacagc acctgtgtgg ttc                                            23

<210> SEQ ID NO 20
<211> LENGTH: 25
<212> TYPE: DNA
<213> ORGANISM: artificial
<220> FEATURE:
<223> OTHER INFORMATION: primer GLUD

<400> SEQUENCE: 20
gctgttcgac aaaacgagga cctgc                                          25

<210> SEQ ID NO 21
<211> LENGTH: 24
<212> TYPE: DNA
<213> ORGANISM: artificial
<220> FEATURE:
<223> OTHER INFORMATION: primer SKRG

<400> SEQUENCE: 21
gaactactgc aattcttaag tcga                                           24

<210> SEQ ID NO 22
<211> LENGTH: 25
<212> TYPE: DNA
<213> ORGANISM: artificial
<220> FEATURE:
<223> OTHER INFORMATION: primer SKRD

<400> SEQUENCE: 22
tagagtcgac ttaagaattg cagta                                          25

<210> SEQ ID NO 23
<211> LENGTH: 26
<212> TYPE: DNA
<213> ORGANISM: artificial
<220> FEATURE:
<223> OTHER INFORMATION: primer GLUD-2

<400> SEQUENCE: 23
cacaggtgct gttcgacaaa acgacc                                         26

<210> SEQ ID NO 24
<211> LENGTH: 4775
<212> TYPE: DNA
<213> ORGANISM: artificial sequence
<220> FEATURE:
<223> OTHER INFORMATION: plasmid p5/ZUINSGly(22A)

<400> SEQUENCE: 24
tagagcgcac gaatgagggc cgacaggaag caaagctgaa aggaatcaaa tttggccgca    60
ggcgtaccgt ggacaggaac gtcgtgctga cgcttcatca gaagggcact ggtgcaacgg   120
```

```
aaattgctca tcagctcagt attgcccgct ccacggttta taaaattctt gaagacgaaa    180
gggcctcgtg atacgcctat ttttataggt taatgtcatg ataataatgg tttcttagac    240
gtcaggtggc acttttcggg gaaatgtgcg cggaacccct atttgtttat ttttctaaat    300
acattcaaat atgtatccgc tcatgagaca ataaccctga taaatgcttc aataatattg    360
aaaaaggaag agtatgagta ttcaacattt ccgtgtcgcc cttattccct tttttgcggc    420
attttgcctt cctgttttg ctcacccaga aacgctggtg aaagtaaaag atgctgaaga    480
tcagttgggt gcacgagtgg gttacatcga actggatctc aacagcggta agatccttga    540
gagttttcgc cccgaagaac gttttccaat gatgagcact tttaaagttc tgctatgtgg    600
cgcggtatta tcccgtgttg acgccgggca agagcaactc ggtcgccgca tacactattc    660
tcagaatgac ttggttgagt actcaccagt cacagaaaag catcttacgg atggcatgac    720
agtaagagaa ttatgcagtg ctgccataac catgagtgat aacactgcgg ccaacttact    780
tctgacaacg atcggaggac cgaaggagct aaccgctttt ttgcacaaca tggggatca    840 tgtaactcgc cttgatcgtt gggaaccgga gctgaatgaa gccataccaa acgacgagcg    900
tgacaccacg atgcctgcag caatggcaac aacgttgcgc aaactattaa ctggcgaact    960
acttactcta gcttcccggc aacaattaat agactggatg gaggcggata agttgcagg    1020 accacttctg cgctcggccc ttccggctgg ctggtttatt gctgataaat ctggagccgg    1080
tgagcgtggg tctcgcggta tcattgcagc actggggcca gatggtaagc cctcccgtat    1140
cgtagttatc tacacgacgg ggagtcaggc aactatggat gaacgaaata gacagatcgc    1200
tgagataggt gcctcactga ttaagcattg gtaactgtca gaccaagttt actcatatat    1260
actttagatt gatttaaaac ttcattttta atttaaaagg atctaggtga agatcctttt    1320
tgataatctc atgaccaaaa tcccttaacg tgagttttcg ttccactgag cgtcagaccc    1380
catcgccgtt ctcgatacgc tgaaccgtgc gcacgctcat cccggacagt tcagcaagct    1440
gctcctggga ccaggcacgc gcaagacgca gcgacctgaa tttgttggta tcactcattt    1500
cctgtctccg aatggaagat ggtcagcaca cagtgttgac cgcgtaatcc tgcgcgacca    1560
cgatcttaac ccgacagtaa cgtgacagcg gtctgacatg ccgcattgag gtctttgaaa    1620
ccgtaacttc agaagcatgt acggtcagat ttaacataag agttcattgt acgcaccgtt    1680
aaaacgcgct cagcgcgctt ctggcgcaaa accgtaaaa atggatgttt ccccgggt    1740 aaaccggaaa aatgcgtcag gaacgctttc agcgcgttgc atgactatgc atgaaactga    1800
atggcgatcg gtttgggcgc gtctgatgcc cataaggcgt attttcggac gttttcagcc    1860
ctgataagaa gaaatcagac tgtagttaca gacgagtcgt gagcgattca ctacgggagt    1920
cgtcggcgag tcatccagta ttttttcctcg cgactctctg gcgactcgcc ttctctgaac    1980
accagagcga cagtgtgttg agtcatcgat aaatcaccga cgactcgttg ccgagtcatc    2040
cagtagtcgc cgacgagccg cttttgtata aatccgaata agaaaatata ttttcaaac    2100 cataacaaca tgatttaaaa agcaaatcag aaaaagtta gttttgcgtg gggtgtgggc    2160
atcctgggaa tgagaacaga ctcgcgtttt tctggaggaa ctgcggggat ttttgattaa    2220
acaatagtca ccgcagagcg gaattttatg caacgctggc tgtgcggcac ggggattttt    2280 aatccccccgg cccgttattc atctccacgg gcgacgggga tacataaacc cgacagcaga    2340
ggacgggtga gcgcgaatcc cagagatgat gaaaaagag gcagagaaac gcgcccaggt    2400
acgttttatc ttattgcttt ggtgttgtcc agggtgtcgg ggctgtgccc tgaccaggtg    2460
gcatttgtct gattgcgcgt gcgcggtccg acaaatgcac atcctgcccc gtcctgtacg    2520
```

```
tgtttttttc accagaacaa cttcacgaag tggcggatga acgctaccaa cgttgccggg    2580
aacgcttcgg cgatgatggc ataacgggct gatacaggca gctcccggag acggacacag    2640
cttgcctgtg agcggatgcc gggagccgac aagcccgtca gggcgcgtca gcgggtttta    2700
gcgggtgtcg gggcgcagcc atgacccagt cacgtagcga tagcggagtg tatactggct    2760
taatatgtta aatcggagtg gtaattcagg gaagtgcttc atgtggcaaa ggaaaaatgt    2820
ggctatcgtg cgtaagtgca acatgtaggt aaaggtgaaa tgacgcctcc tcgctcactc    2880
ggtcgctacg ctcctgccgt gagactgcgg cgggcgttac cggctcacaa ataacgggat    2940
acgcaggcag tgctcaaatc aggaaggacc ggaaaaagga tgcggcgtag ccgttttttcc    3000 ataggctccg ccccctgac aagcatcacg aaatctgacg ctcaaatcag tggcggcgaa    3060
acccgacagg actataaaga tcccaggcgt ttccccctgg tagctccctc gtgcgctctc    3120
ctgttcctgc ctttcggttt accggtgtca ttccgctgtt atggccgcgt ttgtctcatt    3180
ccacgcctga cactcagttc cgggtaggca gttcgctcca gctggactg tatgcacgaa    3240 cccccgttc agtccgacta ccacgcccgt tccggtaact atcaacttga gtccaacccg    3300
gaaagacacg acaaatcgcc agtggcggta gccattggta actgagatgt gcgagagatt    3360
tatctggagt tcttgaagtg ggggcctgag tgcggctaca ctggaaggac agtttaggtg    3420
actcgtctcg cacaagacag ttaccaggtt aagcagttcc ccaactgacc taaccttcga    3480
tcaaaccacc tccccaggtg gttttttcgt tttcagagca agagattacg cgcagaaaaa    3540
aaggatctca agaagatcct ttttacagga gcgattatcg tcttcatcca tgaaggcgtt    3600
tgaagattaa accggcctat ttcatagatc gtaaaatcag ggttttggga tggccgatga    3660
aaccccataa aaacccataa atacatacac ctactaacaa tcatcttttg ctgtaccagg    3720
gtatgaaaag tctcagggtt ccaccccaga atacgccatc aacaagtcct gtcacaccgc    3780
caaataacat gcaaaaaatt gcggatgacc gtaatccggg gtgcagatca atgactgaga    3840
caagtataaa cttcatgcaa aaagtaatta caatcagtcc caaagtcagc ggtgtcccgg    3900
ccctgataat catgccccgga ttatctgaat ttccagcgg gggctgtgag cgccacaacc    3960
tgtatccaag agcggtgcct acgagcagtc ctgccgtcat cattgtaagg cttacgccag    4020
caagttttgt ctcagtgata acaccttatg ctccccatac aaggaaaagt atcgggagaa    4080
aaaacaaacg cccggttgtc atctcccggt cataaagagc agcaaaaccg cgtcgtagta    4140
aaaaagccag caggatcaag cttcagggtt gagatgtgta taagagacag actctagcca    4200
gtttccaagt agaaactaca gtttctaaac tgcaacttttt tctacttttt gcaacttaat    4260
ctattgacta gtcctttata aatgttaaaa catatatata gaaataaata aaaagaggag    4320
gttcatatgc aaatttttgt taaaacttta actggtaaaa ccattacctt agaagttgaa    4380
tcttcagata ccattgataa tgttaaatct aaaattcaag ataaagaagg tattcctcca    4440
gatcaacaag ctctaatatt tgcaggtaaa cagttagaag atggtgctac cctgtctgat    4500
tataacattc agaaagaatc taccttacat ctggtcttag ctctcgctgg tggtcgtttt    4560
gtcaaccagc acctgtgtgg ttctcacctg gttgaagcac tgtacctggt atgtggcgaa    4620
cgtggtttct tctacactcc taaaacaaag cgcggcatcg ttgaacagtg ctgtacctct    4680
atctgttccc tgtaccaact ggagaactac tgcaatggtt aagtcgactc tagctacagc    4740
ctcctttcgg aggctgtttt ttatctcgag gatcc                               4775

<210> SEQ ID NO 25
<211> LENGTH: 4775
```

<212> TYPE: DNA
<213> ORGANISM: artificial sequence
<220> FEATURE:
<223> OTHER INFORMATION: plasmid p6/ZUINSSer(22A)

<400> SEQUENCE: 25

```
tagagcgcac gaatgagggc cgacaggaag caaagctgaa aggaatcaaa tttggccgca      60
ggcgtaccgt ggacaggaac gtcgtgctga cgcttcatca gaagggcact ggtgcaacgg     120
aaattgctca tcagctcagt attgcccgct ccacggttta taaaattctt gaagacgaaa     180
gggcctcgtg atacgcctat ttttataggt taatgtcatg ataataatgg tttcttagac     240
gtcaggtggc acttttcggg gaaatgtgcg cggaacccct atttgtttat ttttctaaat     300
acattcaaat atgtatccgc tcatgagaca ataaccctga taaatgcttc aataatattg     360
aaaaaggaag agtatgagta ttcaacattt ccgtgtcgcc cttattccct ttttttgcggc    420
attttgcctt cctgtttttg ctcacccaga acgctggtg aaagtaaaag atgctgaaga     480
tcagttgggt gcacgagtgg gttacatcga actggatctc aacagcggta agatccttga     540
gagttttcgc cccgaagaac gttttccaat gatgagcact tttaaagttc tgctatgtgg     600
cgcggtatta tcccgtgttg acgccgggca agagcaactc ggtcgccgca tacactattc     660
tcagaatgac ttggttgagt actcaccagt cacagaaaag catcttacgg atggcatgac     720
agtaagagaa ttatgcagtg ctgccataac catgagtgat aacactgcgg ccaacttact     780
tctgacaacg atcggaggac cgaaggagct aaccgctttt ttgcacaaca tgggggatca     840
tgtaactcgc cttgatcgtt gggaaccgga gctgaatgaa gccataccaa acgacgagcg     900
tgacaccacg atgcctgcag caatggcaac aacgttgcgc aaactattaa ctggcgaact     960
acttactcta gcttcccggc aacaattaat agactggatg gaggcggata agttgcagg    1020
accacttctg cgctcggccc ttccggctgg ctggtttatt gctgataaat ctggagccgg    1080
tgagcgtggg tctcgcggta tcattgcagc actggggcca gatggtaagc cctcccgtat    1140
cgtagttatc tacacgacgg ggagtcaggc aactatggat gaacgaaata gacagatcgc    1200
tgagataggt gcctcactga ttaagcattg gtaactgtca gaccaagttt actcatatat    1260
actttagatt gatttaaaac ttcatttta atttaaaagg atctaggtga agatcctttt    1320
tgataatctc atgaccaaaa tcccttaacg tgagttttcg ttccactgag cgtcagaccc    1380
catcgccgtt ctcgatacgc tgaaccgtgc gcacgctcat cccggacagt tcagcaagct    1440
gctcctggga ccaggcacgc gcaagacgca gcgacctgaa tttgttggta tcactcattt    1500
cctgtctccg aatggaagat ggtcagcaca cagtgttgac cgcgtaatcc tgcgcgacca    1560
cgatcttaac ccgacagtaa cgtgacagcg gtctgcatg ccgcattgag gtctttgaaa    1620
ccgtaacttc agaagcatgt acggtcagat ttaacataag agttcattgt acgcaccgtt    1680
aaaacgcgct cagcgcgctt ctggcgcaaa accgtaaaaa atggatgttt ccccccgggt    1740
aaaccggaaa aatgcgtcag gaacgctttc agcgcgttgc atgactatgc atgaaactga    1800
atggcgatcg gtttgggcgc gtctgatgcc cataaggcgt atttttcggac gttttcagcc    1860
ctgataagaa gaaatcagac tgtagttaca dcgagtcgt gagcgattca ctacgggagt    1920
cgtcggcgag tcatccagta ttttcctcg cgactctctg gcgactcgcc ttctctgaac    1980
accagagcga cagtgtgttg agtcatcgat aaatcaccga cgactcgttg ccgagtcatc    2040
cagtagtcgc cgacgagccg cttttgtata aatccgaata agaaaatata ttttcaaac    2100
cataacaaca tgatttaaaa agcaaatcag aaaaagtta gttttgcgtg gggtgtgggc    2160
atcctgggaa tgagaacaga ctcgcgtttt tctgaggaa ctgcggggat ttttgattaa    2220
```

```
acaatagtca ccgcagagcg gaattttatg caacgctggc tgtgcggcac ggggattttt    2280 aatccccgg cccgttattc atctccacgg gcgacgggga tacataaacc cgacagcaga    2340
ggacgggtga gcgcgaatcc cagagatgat gaaaaaagag gcagagaaac gcgcccaggt    2400
acgttttatc ttattgcttt ggtgttgtcc agggtgtcgg ggctgtgccc tgaccaggtg    2460
gcatttgtct gattgcgcgt gcgcggtccg acaaatgcac atcctgcccc gtcctgtacg    2520 tgttttttc accagaacaa cttcacgaag tggcggatga acgctaccaa cgttgccggg    2580
aacgcttcgg cgatgatggc ataacgggct gatacaggca gctcccggag acggacacag    2640
cttgcctgtg agcggatgcc gggagccgac aagcccgtca gggcgcgtca gcgggtttta    2700
gcgggtgtcg gggcgcagcc atgacccagt cacgtagcga tagcggagtg tatactggct    2760
taatatgtta aatcggagtg gtaattcagg gaagtgcttc atgtggcaaa ggaaaaatgt    2820
ggctatcgtg cgtaagtgca acatgtaggt aaaggtgaaa tgacgcctcc tcgctcactc    2880
ggtcgctacg ctcctgccgt gagactgcgg cgggcgttac cggctcacaa ataacgggat    2940
acgcaggcag tgctcaaatc aggaaggacc ggaaaaagga tgcggcgtag ccgttttcc     3000 ataggctccg cccccctgac aagcatcacg aaatctgacg ctcaaatcag tggcggcgaa    3060
acccgacagg actataaaga tcccaggcgt tttccctgg tagctccctc gtgcgctctc     3120
ctgttcctgc ctttcggttt accggtgtca ttccgctgtt atggccgcgt ttgtctcatt    3180
ccacgcctga cactcagttc cgggtaggca gttcgctcca agctggactg tatgcacgaa    3240
ccccccgttc agtccgacta ccacgcccgt tccggtaact atcaacttga gtccaacccg    3300
gaaagacacg acaaatcgcc agtggcggta gccattggta actgagatgt gcgagagatt    3360
tatctggagt tcttgaagtg ggggcctgag tgcggctaca ctggaaggac agtttaggtg    3420
actcgtctcg cacaagacag ttaccaggtt aagcagttcc ccaactgacc taaccttcga    3480
tcaaaccacc tccccaggtg gttttttcgt tttcagagca agagattacg cgcagaaaaa    3540
aaggatctca agaagatcct ttttacagga gcgattatcg tcttcatcca tgaaggcgtt    3600
tgaagattaa accggcctat ttcatagatc gtaaaatcag ggttttggga tggccgatga    3660
aaccccataa aaacccataa atacatacac ctactaacaa tcatcttttg ctgtaccagg    3720
gtatgaaaag tctcagggtt ccaccccaga atacgccatc aacaagtcct gtcacaccgc    3780
caaataacat gcaaaaaatt gcggatgacc gtaatccggg gtgcagatca atgactgaga    3840
caagtataaa cttcatgcaa aaagtaatta caatcagtcc caaagtcagc ggtgtcccgg    3900
ccctgataat catgcccgga ttatctgaat ttctcagcgg gggctgtgag cgccacaacc    3960
tgtatccaag agcggtgcct acgagcagtc ctgccgtcat cattgtaagg cttacgccag    4020
caagttttgt ctcagtgata acaccttatg ctccccatac aaggaaaagt atcgggagaa    4080
aaaacaaacg cccggttgtc atctcccggt cataaagagc agcaaaaccg cgtcgtagta    4140
aaaaagccag caggatcaag cttcagggtt gagatgtgta taagagacag actctagcca    4200
gtttccaagt agaaactaca gtttctaaac tgcaactttt tctactttt gcaacttaat     4260 ctattgacta gtcctttata aatgttaaaa catatatata gaaataaata aaagaggag     4320 gttcatatgc aaattttgt taaaacttta actggtaaaa ccattacctt agaagttgaa     4380
tcttcagata ccattgataa tgttaaatct aaaattcaag ataaagaagg tattccttca    4440
gatcaacaag ctctaatatt tgcaggtaaa cagttagaag atggtgctac cctgtctgat    4500
tataacattc agaagaatc taccttacat ctggtcttag ctctcgctgg tggtcgtttt     4560
gtcaaccagc acctgtgtgg ttctcacctg gttgaagcac tgtacctggt atgtggcgaa    4620
```

```
cgtggtttct tctacactcc taaaacaaag cgcggcatcg ttgaacagtg ctgtacctct    4680
atctgttccc tgtaccaact ggagaactac tgcaatggtt aagtcgactc tagctacagc    4740
ctcctttcgg aggctgtttt ttatctcgag gatcc                               4775
```